(12) United States Patent
Redon et al.

(10) Patent No.: US 10,809,268 B2
(45) Date of Patent: Oct. 20, 2020

(54) METHODS AND KITS FOR MEASURING AND QUANTIFYING DNA DOUBLE-STRANDED BREAKS USING GAMMA-H2AX AND H2AX

(71) Applicant: The United States of America, as represented by the Secretary, Department of Health and Human Services, Bethesda, MD (US)

(72) Inventors: Christophe E. Redon, Rockville, MD (US); William M. Bonner, Washington, DC (US); Yiping Zhang, Boyds, MD (US); Jiuping Ji, Rockville, MD (US)

(73) Assignee: The United States of America, as represented by the Secretary, Department of Health and Human Service, Bethesda, MD (US)

( * ) Notice: Subject to any disclaimer, the term of this patent is extended or adjusted under 35 U.S.C. 154(b) by 245 days.

(21) Appl. No.: 15/545,402

(22) PCT Filed: Feb. 1, 2016

(86) PCT No.: PCT/US2016/016000
§ 371 (c)(1),
(2) Date: Jul. 21, 2017

(87) PCT Pub. No.: WO2016/126616
PCT Pub. Date: Aug. 11, 2016

(65) Prior Publication Data
US 2018/0003720 A1 Jan. 4, 2018

Related U.S. Application Data

(60) Provisional application No. 62/110,764, filed on Feb. 2, 2015.

(51) Int. Cl.
*C12Q 1/6804* (2018.01)
*G01N 33/53* (2006.01)
*G01N 33/68* (2006.01)

(52) U.S. Cl.
CPC ....... *G01N 33/6875* (2013.01); *C12Q 1/6804* (2013.01); *G01N 33/53* (2013.01); *C12Q 2522/101* (2013.01); *C12Q 2523/107* (2013.01)

(58) Field of Classification Search
CPC .. G01N 33/6875; G01N 33/53; C12Q 1/6804; C12Q 2522/101; C12Q 2523/107
See application file for complete search history.

(56) References Cited

U.S. PATENT DOCUMENTS 6,362,317 B1  3/2002  Bonner et al.
6,884,873 B2  4/2005  Bonner et al.
(Continued)

FOREIGN PATENT DOCUMENTS

CN   103399159 A   11/2013
CN   103645327 A   3/2014
WO   WO 01/04158 A1   1/2001

OTHER PUBLICATIONS

Garcia-Canton et al. γH2AX as a novel end-point to detect DNA damage: Applications for the assessment of the in vitro genotoxicity of cigarette smoke. Toxicology in Vitro 26: 1075-1086 (2012).*
(Continued)

*Primary Examiner* — Gailene Gabel
(74) *Attorney, Agent, or Firm* — Leydig, Voit & Mayer, Ltd.

(57) ABSTRACT

Disclosed are methods of measuring the amount of exposure of a host to a DNA double-stranded break (DSB)-causing agent by determining the ratio of the quantity of γ-H2AX to the quantity of total H2AX in a biological sample from the host as compared to the ratio of the quantity of γ-H2AX to
(Continued)

the quantity of total H2AX in a positive control biological sample that has been exposed to a known amount of a DSB-causing agent. Related kits and methods of quantifying DSBs in a test biological sample are also disclosed.

15 Claims, 27 Drawing Sheets

Specification includes a Sequence Listing.

(56) References Cited

U.S. PATENT DOCUMENTS

| | | | |
|---|---|---|---|
| 9,470,694 B2* | 10/2016 | Dertinger | G01N 33/5014 |
| 9,857,358 B2* | 1/2018 | Dertinger | G01N 33/5014 |
| 2008/0145358 A1 | 6/2008 | Zabludoff et al. | |
| 2011/0009387 A1 | 1/2011 | Basso-Porcaro | |

OTHER PUBLICATIONS

Dong et al., "Evaluation of N-acetyl-cysteine against tetrachlorobenzoquinone-induced genotoxicity and oxidative stress in HepG2 cells," *Food Chem. Toxicol.*, 64: 291-297 (2014).

European Patent Office, International Search Report in International Application No. PCT/US2016/016000, dated May 13, 2016.

European Patent Office, Written Opinion in International Application No. PCT/US2016/016000, dated May 13, 2016.

Garcia-Canton et al., "γH2AX as a novel endpoint to detect DNA damage: applications for the assessment of the in vitro genotoxicity of cigarette smoke," *Toxicology In Vitro*, 26(7): 1075-1086 (Jun. 23, 2012).

Ivashkevich et al., "Use of the γ-H2AX assay to monitor DNA damage and repair in translational cancer research," *Cancer Lett.*, 327(1-2): 123-133 (Dec. 31, 2012).

Ji et al., "Phosphorylated fraction of H2AX as a measurement for DNA damage in cancer cells and potential applications of a novel assay," PLoS One, 12(2): e0171582 (Feb. 3, 2017).

Ji et al., "Using γH2AX and H2AX Quantitative ELISA for Monitoring DNA Damage Induced by Chemotherapeutic Agents and Irradiation Exposure," *PowerPoint Slideshow Presented at the ASCO Annual Meeting* (May 30, 2015).

Ji et al., "Using Quantitative γH2AX and H2AX ELISA for Monitoring DNA Damage Induced by Chemotherapeutic Agents and Irradiation Exposure," Poster Presented at the ASCO Annual Meeting (May 30, 2015).

Matsuzaki et al., "Whole cell-ELISA to measure the gammaH2AX response of six aneugens and eight DNA-damaging chemicals," *Mut. Res.*, 700: 71-79 (May 24, 2010).

Moquet et al., "Gamma-H2AX biodosimetry for use in large scale radiation incidents: comparison of a rapid '96 well lyse/fix' protocol with a routine method," *PeerJ*, 2: e282 (Mar. 6, 2014).

Moroni et al., "Evaluation of the Gamma-H2AX Assay for Radiation Biodosimetry in a Swine Model," *Int. J. Mol. Sci.*, 14(7): 14119-14135 (Jul. 8, 2013).

Muslimovic et al., "Measurement of H2AX phosphorylation as a marker of ionizing radiation induced cell damage," *Current Topics in Ionizing Radiation Research Intech*, 3-20 (Feb. 12, 2012).

Redon et al., "Recent developments in the use of γ-H2AX as a quantitative DNA double-strand break biomarker," *Aging*, 3(2): 168-174 (Feb. 11, 2011).

Redon et al., "The use of gamma-H2AX as a biodosimeter for total-body radiation exposure in non-human primates," *PLoS One*, 5(11): e15544-eee15544 (Nov. 23, 2010).

Redon et al., "γ-H2AX and other histone post-translational modifications in the clinic," *Bicohem Biophys Acta.*, 1819(7): 743-756 (Jul. 2012).

Wang et al., "Complex H2AX phosphorylation patterns by multiple kinases including ATM and DNA-PK in human cells exposed to ionizing radiation and treated with kinase inhibitors," *J. Cell. Physiol*, 202: 492-502 (Feb. 2005).

* cited by examiner

METHODS AND KITS FOR MEASURING AND QUANTIFYING DNA DOUBLE-STRANDED BREAKS USING GAMMA-H2AX AND H2AX

CROSS-REFERENCE TO RELATED APPLICATIONS

This patent application is the U.S. national phase of International Patent Application No. PCT/US2016/016000, filed Feb. 1, 2016, which claims the benefit of U.S. Provisional Patent Application No. 62/110,764, filed Feb. 2, 2015, each of which is incorporated by reference in its entirety herein.

STATEMENT REGARDING FEDERALLY SPONSORED RESEARCH AND DEVELOPMENT

This invention was made with Government support under project number Z01ZIABC006140 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,005 Byte ASCII (Text) file named "729119_ST25.txt," dated Jul. 12, 2017.

BACKGROUND OF THE INVENTION

Exposure to ionizing radiation (IR) or other agents may cause DNA double-stranded breaks (DSBs). DNA DSBs may, potentially, damage living cells, tissues, or both, and may result in illness (for example, Acute Radiation Syndrome and cancer), death, or both. Identifying the amount of exposure to a DNA DSB-causing agent may be useful for determining the need for and nature of further testing and/or medical treatment. Accordingly, there is a need for improved methods and kits for measuring the amount of exposure of a host to a DNA DSB-causing agent.

BRIEF SUMMARY OF THE INVENTION

An embodiment of the invention provides a method of measuring the amount of exposure of a host to a DNA DSB-causing agent, the method comprising: contacting (i) a first portion of a positive control biological sample and (ii) a first portion of a biological sample from the host with an antibody or antigen binding fragment thereof that specifically binds to gamma (γ)-H2AX and forms a first complex with the γ-H2AX; contacting (i) a second portion of the positive control biological sample and (ii) a second portion of the biological sample from the host with an antibody or antigen binding fragment thereof that specifically binds to an H2A core protein and forms a second complex with the H2A core protein, wherein the positive control biological sample has been exposed to a known amount of the DSB-causing agent; contacting the first and second complexes of the positive control biological sample and the biological sample from the host with an antibody or antigen binding fragment thereof that specifically binds to H2AX and forms a third complex with H2AX in the first complex and forms a fourth complex with H2AX in the second complex; detecting the third and fourth complexes in the positive control biological sample and the biological sample from the host; quantifying the third and fourth complexes in the positive control biological sample and the biological sample from the host; determining a ratio of the quantity of the third complex to the quantity of the fourth complex in the positive control biological sample; determining a ratio of the quantity of the third complex to the quantity of the fourth complex in the biological sample from the host; and comparing the ratio of the quantity of the third complex to the quantity of the fourth complex in the positive control biological sample to the ratio of the quantity of the third complex to the quantity of the fourth complex in the biological sample from the host to determine the amount of exposure of the host to the DNA DSB-causing agent.

Another embodiment of the invention provides a method of quantifying DNA DSBs in a test biological sample, the method comprising: contacting (i) a first portion of a positive control biological sample and (ii) a first portion of a test biological sample with an antibody or antigen binding fragment thereof that specifically binds to γ-H2AX and forms a first complex with the γ-H2AX; contacting (i) a second portion of the positive control biological sample and (ii) a second portion of the test biological sample with an antibody or antigen binding fragment thereof that specifically binds to an H2A core protein and forms a second complex with the H2A core protein, wherein the positive control biological sample has a known quantity of DSBs; contacting the first and second complexes of the positive control biological sample and the test biological sample with an antibody or antigen binding fragment thereof that specifically binds to H2AX and forms a third complex with H2AX in the first complex and forms a fourth complex with H2AX in the second complex; detecting the third and fourth complexes in the positive control biological sample and the test biological sample; quantifying the third and fourth complexes in the positive control biological sample and the test biological sample; determining a ratio of the quantity of the third complex to the quantity of the fourth complex in the positive control biological sample; determining a ratio of the quantity of the third complex to the quantity of the fourth complex in the test biological sample; and comparing the ratio of the quantity of the third complex to the quantity of the fourth complex in the positive control biological sample to the ratio of the quantity of the third complex to the quantity of the fourth complex in the test biological sample to determine the quantity of DSBs in the test biological sample.

Another embodiment of the invention provides a kit comprising: at least one substrate; an antibody or antigen binding fragment thereof that specifically binds to γ-H2AX; an antibody or antigen binding fragment thereof that specifically binds to H2A core protein; an antibody or antigen binding fragment thereof that specifically binds to H2AX; and a detecting agent comprising a label.

Still another embodiment of the invention provides a method of testing compounds for ability to cause DNA DSBs in a host, the method comprising: (a) administering a test compound to a host; (b) obtaining a biological sample from the host after the host has been administered the test compound; (c) contacting (i) a first portion of a control biological sample and (ii) a first portion of the host biological sample with an antibody or antigen binding fragment thereof that specifically binds to γ-H2AX and forms a first complex with the γ-H2AX; (d) contacting (i) a second portion of the control biological sample and (ii) a second portion of the host biological sample with an antibody or antigen binding fragment thereof that specifically binds to an H2A core protein and forms a second complex with the H2A core protein, wherein the control biological sample has not been exposed to the test compound; (e) contacting the first and second complexes of the control biological sample and the host biological sample with an antibody or antigen binding fragment thereof that specifically binds to H2AX and forms a third complex with H2AX in the first complex and forms a fourth complex with H2AX in the second complex; (f) detecting the third and fourth complexes in the control biological sample and the host biological sample; (g) quantifying the third and fourth complexes in the control biological sample and the host biological sample; (h) determining a ratio of the quantity of the third complex to the quantity of the fourth complex in the control biological sample; (i) determining a ratio of the quantity of the third complex to the quantity of the fourth complex in the host biological sample; and (j) comparing the ratio of the quantity of the third complex to the quantity of the fourth complex in the control biological sample to the ratio of the quantity of the third complex to the quantity of the fourth complex in the host biological sample, wherein an increase in the ratio in the host biological sample as compared to the ratio in the control biological sample indicates that the test compound has the ability to cause DNA DSBs in the host.

Another embodiment of the invention provides a method of screening test compounds for ability to cause DNA DSBs, the method comprising: (a) dividing a population of test biological samples into more than one test sub-population; (b) treating each test sub-population with a test compound, wherein each test sub-population is treated with a different test compound; (c) contacting (i) a first portion of each treated test sub-population and (ii) a first portion of a control biological sample with an antibody or antigen binding fragment thereof that specifically binds to γ-H2AX and forms a first complex with the γ-H2AX; (d) contacting (i) a second portion of each treated test sub-population and (ii) a second portion of a control biological sample with an antibody or antigen binding fragment thereof that specifically binds to an H2A core protein and forms a second complex with the H2A core protein; wherein the control biological sample has not been treated with a test compound; (e) contacting the first and second complexes of the control biological sample and the treated test sub-populations with an antibody or antigen binding fragment thereof that specifically binds to H2AX and forms a third complex with H2AX in the first complex and forms a fourth complex with H2AX in the second complex; (f) detecting the third and fourth complexes in the control biological sample and the treated test sub-populations; (g) quantifying the third and fourth complexes in the control biological sample and the treated test sub-populations; (h) determining a ratio of the quantity of the third complex to the quantity of the fourth complex in the control biological sample; (i) determining a ratio of the quantity of the third complex to the quantity of the fourth complex in the treated test sub-populations; and (j) comparing the ratio of the quantity of the third complex to the quantity of the fourth complex in the control biological sample to the ratio of the quantity of the third complex to the quantity of the fourth complex in the treated test sub-populations, wherein an increase in the ratio in a treated test sub-population as compared to the ratio in the control biological sample indicates that the test compound has the ability to cause DNA DSBs.

An embodiment of the invention provides a method of testing compounds for ability to cause DNA DSBs in a host, the method comprising: (a) contacting (i) a first portion of a control biological sample and (ii) a first portion of a host biological sample with an antibody or antigen binding fragment thereof that specifically binds to γ-H2AX and forms a first complex with the γ-H2AX, wherein the host biological sample is from a host which has been administered a test compound; (b) contacting (i) a second portion of the control biological sample and (ii) a second portion of the host biological sample with an antibody or antigen binding fragment thereof that specifically binds to an H2A core protein and foul's a second complex with the H2A core protein, wherein the control biological sample has not been exposed to the test compound; (c) contacting the first and second complexes of the control biological sample and the host biological sample with an antibody or antigen binding fragment thereof that specifically binds to H2AX and forms a third complex with H2AX in the first complex and forms a fourth complex with H2AX in the second complex; (d) detecting the third and fourth complexes in the control biological sample and the host biological sample; (e) quantifying the third and fourth complexes in the control biological sample and the host biological sample; (f) determining a ratio of the quantity of the third complex to the quantity of the fourth complex in the control biological sample; and (g) determining a ratio of the quantity of the third complex to the quantity of the fourth complex in the host biological sample; (h) comparing the ratio of the quantity of the third complex to the quantity of the fourth complex in the control biological sample to the ratio of the quantity of the third complex to the quantity of the fourth complex in the host biological sample, wherein an increase in the ratio in the host biological sample as compared to the ratio in the control biological sample indicates that the test compound has the ability to cause DNA DSBs in the host.

BRIEF DESCRIPTION OF THE SEVERAL VIEWS OF THE DRAWINGS

FIGS. 9A-9C: Bone marrow samples were obtained from patients undergoing treatment before drug administration (0), and 4 hours (hr) after drug administration on day 1 (D1 4) and day 4 (D4 4). FIGS. 9D-F: Tumor biopsies were obtained before (pre) and after drug administration (post).

DETAILED DESCRIPTION OF THE INVENTION

Figures 1A, 1B:
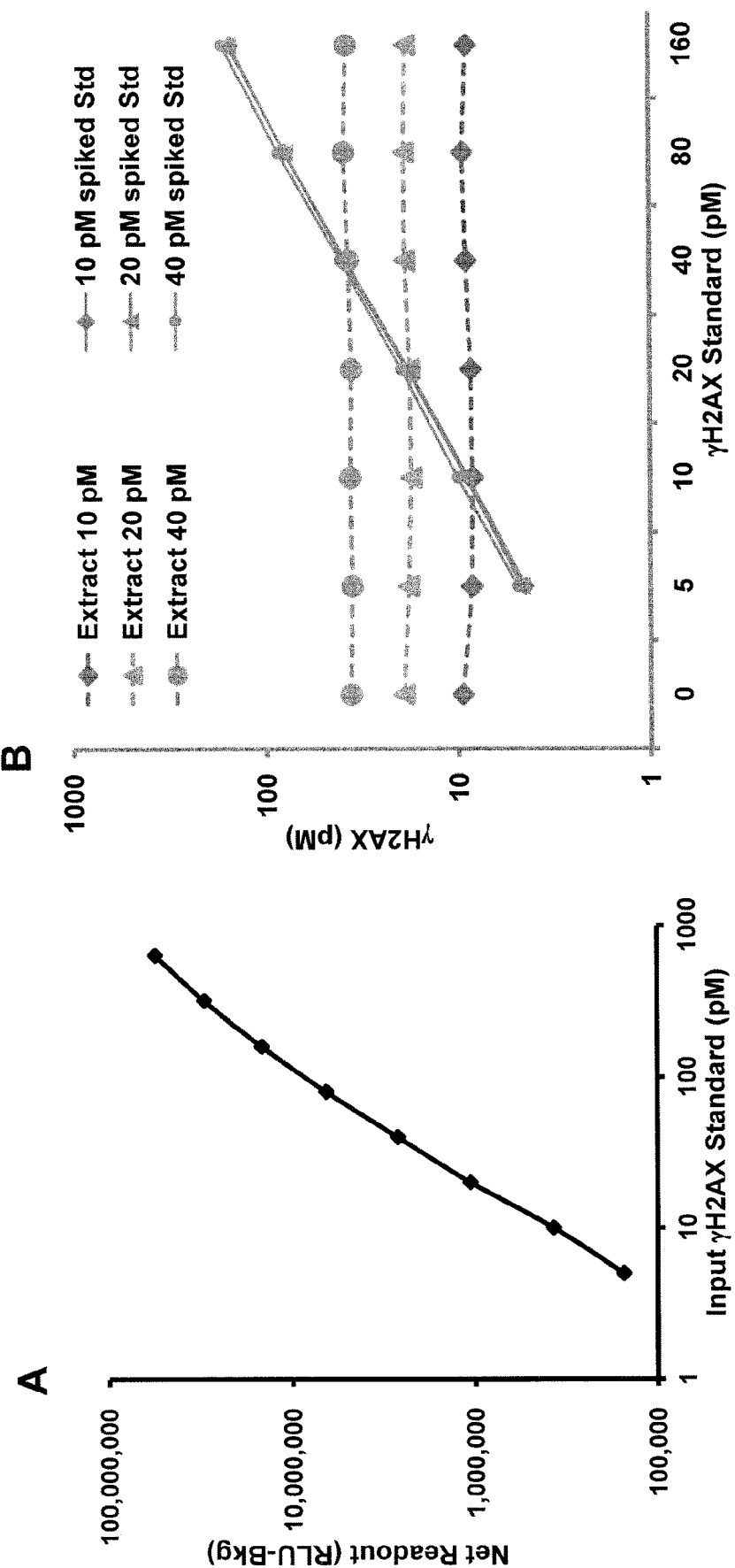
FIG. 1A is a graph (standard curve) showing the net readout (Relative Light Units (RLU) minus (−) Background (Bkg)) detecting various concentrations of γ-H2AX (pM) using chemiluminescent enzyme-linked immunosorbant assay (ELISA). Samples contained the standard γH2AX peptide at zero, 5, 10, 20, 40, 80, 160, 320 and 640 pM. The background (Bkg) with zero pM standard is about 500,000 RLU.
FIG. 1B is a graph showing the independence of standard curve values on sample composition. A well-characterized and quantified extract was diluted to 10 pM (diamonds), 20 pM (triangles), or 40 pM (circles) γ-H2AX. Aliquots of each dilution were spiked with amounts of the standard γH2AX peptide to 5, 10, 20, 40, 80, and 160 pM. After the assay, the readouts were converted to γH2AX peptide concentrations. Solid lines represent measured values of γH2AX peptide concentrations after subtraction of input extract concentrations. Dashed lines represent measured values of extract concentrations of γH2AX after subtraction of input standard concentrations.

The methods and kits of the invention provide many advantages. For example, because the inventive methods and kits quantify both γ-H2AX and total H2AX, the inventive methods and kits may provide an accurate biodosimetric measurement of the amount of exposure of a host to a DNA DSB-causing agent. The inventive methods and kits also may provide the ratio of γ-H2AX to total H2AX in a sample independent of any one or more of cell type, cell number, cell viability, cell lysis efficiency, and laboratory operator variability. In the inventive methods and kits, total H2AX may advantageously serve as an internal control that may account for differences in sample quality that may have arisen due to any one or more of specimen collection, storage, shipping, sample processing, extract preparation, and ELISA testing. Other advantages that may be provided by the inventive methods and kits include any one or more of lower background signals, greater sensitivity, and the ability to test patient tissue samples. The inventive methods and kits may provide a quantitative range of about 100-fold for both γ-H2AX and total H2AX. The inventive methods and kits may also provide a sensitivity of at least about 5 pM for γ-H2AX and at least about 50 pM for total H2AX. The inventive methods and kits may also advantageously measure an actual amount of protein (e.g., actual pictograms) as opposed to merely providing relative values of proteins. In addition, the inventive methods and kits may employ an immobilized antibody or antigen binding fragment thereof to capture total H2A core protein and γ-H2AX, which may reduce or eliminate the need to purify the antigen from complex mixtures prior to analysis, which may simplify the methods and increase the specificity and sensitivity of the methods. Moreover, the inventive methods and kits may provide a standardized clinical assay that can be used as a biodosimeter. The inventive methods may, advantageously, be completed rapidly (for example, within about one working day, less than about one working day, or more than about one working day). The inventive methods may, advantageously screen agents for the ability to cause DNA DSB after a short treatment with the agent(s) to be screened in vitro (e.g., about 1 hr, less than about 1 hr, more than about 1 hr). The inventive methods may, for example, be suitable for high-throughput screening (for example, about 100 to about 5000 cells per well) and may be carried out using a plate-based immunoassay, for example, a 96/384 plate-based immunoassay. Because the cell extract employed in the inventive methods may also be used for additional, conventional immunoassays such as, for example Western Blot (WB), the inventive methods and kits may also be compatible with other, additional assays in order to, for example, further identify potential downstream targets and carry out mechanistic and molecular studies (e.g., PARP1 assays, Top1 assays, and LUMINEX protein assays for apoptosis (Invitrogen, Waltham, Mass.)). Without being bound to a particular theory or mechanism, it is also believed that because γ-H2AX forms at a biological endpoint as opposed to an intermediate biochemical step, the inventive methods provide a more comprehensive measurement of DNA DSB because the inventive methods cover γ-H2AX formed by multiple biochemical enzymatic targets and pathways.

The inventive methods and kits may also advantageously overcome one or more obstacles to obtaining an accurate biodosimetric measurement using other methods such as those that involve counting "nuclear foci" through a microscope. "Nuclear foci" refer to areas surrounding the DSB, which may be microscopically detected and counted using an anti-γ-H2AX antibody. However, because each focus contains a certain percentage of the total nuclear H2AX, and the total H2AX content may vary from cell type to cell type, methods that involve counting nuclear foci lack the total H2AX value necessary to convert those data into biodosimetric measurements. The inventive methods and kits may advantageously overcome one or more of these obstacles.

An embodiment of the invention provides a method of measuring the amount of exposure of a host to a DNA DSB-causing agent. The DNA DSB-causing agent may be any agent that causes DNA DSBs. Non-limiting examples of DNA DSB-causing agents include IR (such as, for example, X-rays and gamma rays), environmental agents such as, for example, ultraviolet (UV) light, reactive oxygen species, mutagenic chemicals, cigarette smoke, and radiation from, for example, cell phones, and drugs such as, for example, anti-cancer agents (e.g., bleomycin and topotecan).

In response to DSB formation, cells phosphorylate the histone protein H2AX. In this regard, the method may comprise contacting (i) a first portion of a positive control biological sample and (ii) a first portion of a biological sample from the host with an antibody or antigen binding fragment thereof that specifically binds to phosphorylated H2AX (gamma (γ)-H2AX) and forms a first complex with the γ-H2AX.

The biological samples (from the host and the positive control biological sample) may comprise any suitable biological sample. The biological samples can comprise any solubilized homogenate or extract from any suitable biological material. Non-limiting examples include tissues, serum, plasma, urine, sputum, saliva, whole cells, cell lysate, or a fraction of the cell lysates, e.g., a nuclear or cytoplasmic fraction, a whole protein fraction, or an acid extract of histones. If the sample comprises whole cells, the cells can be any cells of the host, e.g., the cells of any organ or tissue, including blood cells or cancer cells. In an embodiment of the invention, the cells may be hair bulb cells. Hair bulbs contain dividing cells and are believed to be more sensitive to drug effects. In an embodiment of the invention, the source material may be from any eukaryotic source such as, for example, invertebrates (such as, for example, yeast), and vertebrates. Preferably, the biological samples comprise cell lysate. In an embodiment of the invention, the biological samples comprise cell lysate from no more than a single cell type. In another embodiment of the invention, the biological samples comprise cell lysates from two or more cell types, for example, normal and abnormal tissues, such as those in a tumor biopsy. In an embodiment of the invention, the biological sample is a cancer cell or a lysate of a cancer cell. Regardless of the origin or composition of the biological sample from the host, the positive control biological sample is preferably identical to the biological sample from the host with the exception that the positive control biological sample has been exposed to a known amount of the DSB-causing agent.

The host may be any eukaryote such as, for example, an invertebrate (such as, for example, yeast) or vertebrate. Mammals are the preferred host. The mammalian host may be, for example, of the order Rodentia, such as mice and hamsters, or of the order Logomorpha, such as rabbits. The host may be from the order Carnivora, including Felines (cats) and Canines (dogs). The host may be from the order Artiodactyla, including Bovines (cows) and Swines (pigs) or of the order Perssodactyla, including Equines (horses). The host may be of the order Primates, Ceboids, or Simoids (monkeys) or of the order Anthropoids (humans and apes). Most preferably, the host is a human.

The antibody and antigen binding fragment thereof that specifically bind to γ-H2AX are also collectively referred to herein as "anti-γ-H2AX antibody" or "anti-γ-H2AX antibodies." The anti-γ-H2AX antibody binds to γ-H2AX with measurably higher affinity to γ-H2AX than to other molecules. In an embodiment of the invention, the anti-γ-H2AX antibody may specifically bind to the carboxyl terminus of γ-H2AX (SEQ ID NO: 1, wherein the serine in the first position of SEQ ID NO: 1 is phosphorylated), and does not bind to the carboxyl terminus of non-phosphorylated H2AX (SEQ ID NO: 3, wherein the serine in the first position of SEQ ID NO: 3 is not phosphorylated). In an embodiment of the invention, the anti-γ-H2AX antibody may specifically bind to γ-H2AX (SEQ ID NO: 2, wherein the serine at position 27 of SEQ ID NO: 2 is phosphorylated), and does not bind to non-phosphorylated H2AX (SEQ ID NO: 4, wherein the serine at position 27 of SEQ ID NO: 3 is not phosphorylated). Suitable anti-γ-H2AX antibodies are described in U.S. Pat. Nos. 6,884,873 and 6,362,317, each of which is incorporated by reference herein in its entirety. Anti-γ-H2AX antibodies are also commercially available (from, for example, Millipore (Billerica, Mass.)).

While the contacting may take place in vitro or in vivo with respect to the host, preferably, the contacting is in vitro. Contacting a biological sample with the anti-γ-H2AX antibody may comprise physically contacting the biological sample with the anti-γ-H2AX antibody such that the anti-γ-H2AX antibody binds to γ-H2AX that is present in the sample. The binding of the anti-γ-H2AX antibody to the γ-H2AX forms a first complex that comprises the γ-H2AX bound to the anti-γ-H2AX antibody.

The method may further comprise contacting (i) a second portion of the positive control biological sample and (ii) a second portion of the biological sample from the host with an antibody or antigen binding fragment thereof that specifically binds to an H2A core protein and forms a second complex with the H2A core protein. The antibody and antigen binding fragment thereof that specifically bind to the H2A core protein are also collectively referred to herein as "anti-H2A core protein antibody" or "anti-H2A core protein antibodies." The anti-H2A core protein antibody binds to H2A core protein with measurably higher affinity to H2A core protein than to other molecules. In an embodiment of the invention, the anti-H2A core protein antibody specifically binds to H2A core protein that is present in the sample, such as, for example, H2A1, H2A2, H2AX (both phosphorylated and non-phosphorylated), and H2AZ. In this regard, the anti-H2A core protein antibody captures all H2A proteins that are present in the biological sample (total H2A), including H2AX (both phosphorylated and non-phosphorylated). Accordingly, the second complex may comprise anti-H2A core protein antibody bound to phosphorylated or non-phosphorylated H2AX. Anti-H2A core protein antibodies are commercially available from companies such as, for example, Novus (St. Charles, Mo.).

Contacting a biological sample with the anti-H2A core protein antibody may comprise physically contacting the biological sample with the anti-H2A core protein antibody such that the anti-H2A core protein antibody binds to H2A core protein that is present in the sample. The binding of the anti-H2A core protein antibody with the anti-H2A core protein forms a second complex that comprises the H2A core protein bound to the anti-H2A core protein antibody.

The contacting of the biological sample(s) with the anti-γ-H2AX antibody and the contacting of the biological sample(s) with the anti-H2A core protein antibody may take place simultaneously or in any sequence. In an embodiment of the invention, a substrate such as, for example, a multi-well plate, is coated with both the anti-γ-H2AX antibody and the anti-H2A core protein antibody. Preferably, the anti-γ-H2AX antibody and the anti-H2A core protein antibody are applied to separate wells of a multi-well plate. A biological sample may be added to the coated surfaces of the wells so that the anti-γ-H2AX antibody and the anti-H2A core protein antibody specifically bind to their respective antigens simultaneously or sequentially. In an embodiment of the invention, the anti-γ-H2AX antibody and the anti-H2A core protein antibody are coated onto separate substrates. A portion of a biological sample may be added to the coated surface of each substrate so that anti-γ-H2AX antibody and the anti-H2A core protein antibody specifically bind to their respective antigens simultaneously or sequentially. In an embodiment of the invention, the method comprises contacting the biological sample(s) with the anti-γ-H2AX antibody prior to contacting of the biological sample(s) with the anti-H2A core protein antibody. In another embodiment of the invention, the method comprises contacting the biological sample(s) with the anti-γ-H2AX antibody after contacting of the biological sample(s) with the anti-H2A core protein antibody.

In an embodiment of the invention, the method comprises washing any unbound anti-γ-H2AX antibody and any unbound anti-H2A core protein antibody from the first and second complexes, respectively.

The method may further comprise contacting the first and second complexes of the positive control biological sample and the biological sample from the host with an antibody or antigen binding fragment thereof that specifically binds to H2AX and forms a third complex with H2AX in the first complex and forms a fourth complex with H2AX in the second complex. The antibody and antigen binding fragment thereof that specifically bind to H2AX are also collectively referred to herein as "anti-H2AX antibody" or "anti-H2AX antibodies." The anti-H2AX antibody binds H2AX with measurably higher affinity to H2AX than to other molecules. In an embodiment of the invention, the anti-H2AX antibody specifically binds to H2AX that is present in the sample, including phosphorylated H2AX and non-phosphorylated H2AX. In this regard, the anti-H2AX antibody captures all H2AX proteins that are present in the biological sample (total H2AX). Anti-H2AX antibodies for most mammals are commercially available (for example, Abcam (San Francisco, Calif.)).

Contacting the first and second complexes with the anti-H2AX antibody may comprise physically contacting the first and second complexes with the anti-H2AX antibody such that the anti-H2AX antibody binds to any H2AX that is present in the first and second complexes. The binding of the anti-H2AX antibody to the first complex forms a third complex that comprises the H2AX of the first complex bound to the anti-H2AX antibody. The binding of the anti-H2AX antibody to the second complex forms a fourth complex that comprises the H2AX of the second complex bound to the anti-H2AX antibody. In this regard, the fourth complex comprises the anti-H2AX antibody bound to any phosphorylated or non-phosphorylated H2AX that was captured by the anti-H2A core protein antibody.

The contacting of the first and second complexes with the anti-H2AX antibody may take place simultaneously or in any sequence. In an embodiment of the invention, the method may comprise contacting the first complex with the anti-H2AX antibody prior to contacting the second complex with the anti-H2AX antibody. In another embodiment of the invention, the method may comprise contacting the first complex with the anti-H2AX antibody after contacting the second complex with the anti-H2AX antibody.

In an embodiment of the invention, the method comprises washing any unbound anti-H2AX antibody from the third and fourth complexes, respectively.

The method further comprises detecting the third and fourth complexes in the positive control biological sample and the biological sample from the host. The third and fourth complexes may be detected in any suitable manner known in the art. In an embodiment of the invention, detecting the third and fourth complexes in the biological samples(s) comprises contacting each of the third and fourth complexes with a detecting agent. The detecting agent may comprise, for example, an antibody or antigen binding fragment thereof that specifically binds to the third and fourth complex, respectively (hereinafter referred to collectively as "detection antibody" or "detection antibodies"). The third and fourth complexes may be detected using the same detection antibody or different detection antibodies. The detection antibody binds to the third or fourth complex (or both) with measurably higher affinity to the third or fourth complex (or both) than to other molecules. In an embodiment of the invention, the detection antibody specifically binds to the anti-H2AX antibody.

In an embodiment of the invention, the detection antibody comprises a detectable label. The detectable label may be any suitable detectable label that provides a detectable signal. Non-limiting examples of detectable labels include enzymes (e.g., alkaline phosphatase, horseradish peroxidase), fluorescent molecules (e.g., fluorescein isothiocyanate (FITC), phycoerythrin (PE)), luminescent molecules, dyes, biotin, and element particles (e.g., gold particles). When the detectable label is an enzyme, the method may further comprise adding a substrate to the third and fourth complexes that is catalyzed by the enzyme to produce a detectable signal. In an embodiment of the invention, the detectable signal may be amplified and/or visually detected. For example, acetylcholinesterase-catalyzed hydrolysis may be useful for colorimetric detection through gold or silver nanoparticle aggregation.

The antibodies for use in the inventive methods, including the anti-γ-H2AX antibody, the anti-H2A core protein antibody, the anti-H2AX antibody, and the detection antibody, can be of any type. For instance, any of the antibodies can be of any isotype, e.g., IgA, IgD, IgE, IgG, IgM, etc. Any of the antibodies can be monoclonal or polyclonal. Any of the antibodies can be a naturally-occurring antibody, e.g., an antibody isolated and/or purified from a mammal, e.g., mouse, rabbit, goat, horse, chicken, hamster, human, etc. Alternatively, any of the antibodies can be a genetically-engineered antibody, e.g., a humanized antibody or a chimeric antibody. Any of the antibodies can be in monomeric or polymeric form.

In an embodiment of the invention, the methods may employ an antigen binding fragment of any of the antibodies described herein. The antigen binding fragment can be any portion of the antibody that has at least one antigen binding site. In an embodiment, the antigen binding fragment is a Fab fragment (Fab), F(ab')2 fragment, diabody, triabody, tetrabody, single-chain variable region fragment (scFv), or disulfide-stabilized variable region fragment (dsFv). A single-chain variable region fragment (scFv), which is a truncated Fab fragment including the variable (V) domain of an antibody heavy chain linked to a V domain of a light antibody chain via a synthetic peptide, can be generated using routine recombinant DNA technology techniques (see, e.g., Murphy et al. (eds.), *Murphy's Immunobiology*, 8$^{th}$ Ed., Garland Science, New York, N.Y. (2014)). Similarly, disulfide-stabilized variable region fragments (dsFv) can be prepared by recombinant DNA technology. In an embodiment of the invention, the antigen binding fragment of the antibody that specifically binds to γ-H2AX, H2A core protein, or H2AX is a Fab fragment (Fab), F(ab')2 fragment, diabody, triabody, tetrabody, single-chain variable region fragment (scFv), or disulfide-stabilized variable region fragment (dsFv). The antigen binding fragments that may be useful in the methods of the invention, however, are not limited to these exemplary types of antibody fragments.

In an embodiment of the invention, the method comprises washing any unbound detection antibody from the third and fourth complexes, respectively.

The method further comprises quantifying the third and fourth complexes in the positive control biological sample and the biological sample from the host. The third and fourth complexes may be quantified in any suitable manner known in the art. In an embodiment of the invention, quantifying the third and fourth complexes comprises determining the amount of detectable label present. For example, the method may comprise determining the amount of fluorescence or luminescence provided by the detectable label.

The method further comprises determining a ratio of the quantity of the third complex to the quantity of the fourth complex in the positive control biological sample; determining a ratio of the quantity of the third complex to the quantity of the fourth complex in the biological sample from the host; and comparing the ratio of the quantity of the third complex to the quantity of the fourth complex in the positive control biological sample to the ratio of the quantity of the third complex to the quantity of the fourth complex in the biological sample from the host to determine the amount of exposure of the host to the DNA DSB-causing agent. Because the positive control biological sample was exposed to a known amount of a DNA DSB-causing agent, comparing the ratio of the quantity of the third complex to the quantity of the fourth complex in the positive control biological sample to the same in the biological sample from the host provides the amount of exposure of the host to a DNA DSB-causing agent.

Another embodiment of the invention provides a method of quantifying DNA DSBs in a test biological sample. The method may comprise contacting (i) a first portion of a positive control biological sample and (ii) a first portion of a test biological sample with an antibody or antigen binding fragment thereof that specifically binds to γ-H2AX and forms a first complex with the γ-H2AX. The test biological sample may be any suitable test biological sample. For example, the test biological sample may be a biological sample from a host, as described herein with respect to other aspects of the invention. In an embodiment, the positive control biological sample may also be as described herein with respect to other aspects of the invention except that the positive control biological sample has a known quantity of DSBs. The anti-γ-H2AX antibody, the first complex, and the contacting of the anti-γ-H2AX antibody with the biological samples may be as described with respect to other aspects of the invention.

The method of quantifying DNA DSBs in a test biological sample may further comprise contacting (i) a second portion of the positive control biological sample and (ii) a second portion of the test biological sample with an antibody or antigen binding fragment thereof that specifically binds to an H2A core protein and forms a second complex with the H2A core protein. The anti-H2A core protein antibody, the second complex, and the contacting of the anti-H2A core protein antibody with the biological samples may be as described with respect to other aspects of the invention.

In an embodiment of the invention, the method of quantifying DNA DSBs in a test biological sample further comprises washing any unbound anti-γ-H2AX antibody and any unbound anti-H2A core protein antibody from the first and second complexes, respectively.

The method of quantifying DNA DSBs in a test biological sample may further comprise contacting the first and second complexes of the positive control biological sample and the test biological sample with an antibody or antigen binding fragment thereof that specifically binds to H2AX and forms a third complex with H2AX in the first complex and forms a fourth complex with H2AX in the second complex. The anti-H2AX antibody, the third and fourth complexes, and the contacting of the anti-H2AX antibody with the first and second complexes may be as described herein with respect to other aspects of the invention.

In an embodiment of the invention, the method of quantifying DNA DSBs in a test biological sample further comprises washing any unbound anti-H2AX antibody from the third and fourth complexes, respectively.

The method of quantifying DNA DSBs in a test biological sample may further comprise detecting the third and fourth complexes in the positive control biological sample and the test biological sample; quantifying the third and fourth complexes in the positive control biological sample and the test biological sample; determining a ratio of the quantity of the third complex to the quantity of the fourth complex in the positive control biological sample; and determining a ratio of the quantity of the third complex to the quantity of the fourth complex in the test biological sample. Detecting the third and fourth complexes, quantifying the third and fourth complexes, and determining the ratio of the quantity of the third complex to the quantity of the fourth complex may be carried out as described herein with respect to other aspects of the invention.

The method may further comprise comparing the ratio of the quantity of the third complex to the quantity of the fourth complex in the positive control biological sample to the ratio of the quantity of the third complex to the quantity of the fourth complex in the test biological sample to determine the quantity of DSBs in the test biological sample. Because the positive control biological sample has a known quantity of DSBs, comparing the ratio of the quantity of the third complex to the quantity of the fourth complex in the positive control biological sample to the ratio of the quantity of the third complex to the quantity of the fourth complex in the test biological sample provides the quantity of DSBs in the test biological sample.

Another embodiment of the invention provides a kit that may be useful for measuring the amount of exposure of a host to a DNA DSB-causing agent and/or quantifying DNA DSBs in a test biological sample. The kit may comprise at least one substrate. For example, the kit may comprise one, two, three four, five, six, or more substrates. Preferably, the kit comprises two substrates, including a first substrate for testing a test biological sample or a biological sample from a host and a second substrate for testing a positive control biological sample. In an embodiment of the invention, the substrate is a plate, e.g., a multiwell plate.

The kit may further comprise an antibody or antigen binding fragment thereof that specifically binds to γ-H2AX, an antibody or antigen binding fragment thereof that specifically binds to H2A core protein, and an antibody or antigen binding fragment thereof that specifically binds to H2AX. The anti-γ-H2AX, anti-H2A core protein, and anti-H2AX antibodies and antigen binding fragments thereof may be as described herein with respect to other aspects of the invention. In an embodiment of the invention, the antigen binding fragment of the antibody that specifically binds to γ-H2AX, H2A core protein, or H2AX is a Fab fragment (Fab), F(ab')2 fragment, diabody, triabody, tetrabody, single-chain variable region fragment (scFv), or disulfide-stabilized variable region fragment (dsFv).

In an embodiment of the invention, the anti-γ-H2AX and anti-H2A core protein antibody is affixed to the at least one substrate. For example, the kit may comprise a first substrate comprising an anti-γ-H2AX antibody affixed thereto and a second substrate comprising an anti-H2A core protein antibody affixed thereto. In an embodiment of the invention, the kit comprises a single substrate comprising both anti-γ-H2AX and anti-H2A core protein antibodies affixed thereto. For example, when the substrate is a multiwell plate, anti-γ-H2AX antibody may be affixed to each of a first set of one or more wells of the multiwell plate and anti-H2A core protein antibody may be affixed to a second set of one or more wells of the multiwell plate. In this regard, the substrate may be a multiwell plate in which the anti-γ-H2AX antibody and the anti-H2A core protein antibody are affixed to separate wells.

The kit may further comprise a detecting agent comprising a label. The detecting agent may be a detection antibody as described herein with respect to other aspects of the invention. In this regard, the detecting agent may be an antibody or antigen binding fragment thereof that specifically binds to the antibody or antigen binding fragment thereof that specifically binds to H2AX. The label may also be as described herein with respect to other aspects of the invention. For example, the label may be an enzyme, a fluorescent molecule, a dye, or biotin.

The kit may further comprise a reagent for facilitating the binding of one or more of the anti-γ-H2AX antibody, anti-H2A core protein antibody, and anti-H2AX antibody to the γ-H2AX, H2A core protein, and H2AX, respectively. The kit may further comprise a reagent for facilitating detection of the detecting agent (e.g., a substrate that reacts with an enzyme to provide a detectable signal). The kit may further comprise one or more protamines (small nuclear proteins) which may, advantageously, decrease non-specific binding and/or increase signal-to-background ratio. The kit may also comprise other materials and reagents commonly employed in immunochemical test kits.

Because many drugs, such as anti-cancer agents, cause DNA DSBs, the inventive methods and kits may be useful for monitoring drug therapies, such as anti-cancer therapy, in a patient. Quantifying DNA DSBs or measuring the amount of exposure of a host to a DNA DSB-causing agent according to the inventive methods may, for example, indicate a need to increase or decrease the dosage of the drug, e.g., anti-cancer agent.

Another embodiment of the invention provides a method of screening test compounds for ability to cause DNA DSBs. The method may comprise dividing a population of test biological samples into more than one test sub-population. In an embodiment, the test biological samples are divided into at least two sub-populations. Dividing the test biological samples into more than one sub-population may be carried out in any suitable manner. For example, the test biological samples may be divided by being placed in different wells of multi-well plates. The test biological sample may be as described herein with respect to other aspects of the invention.

The method may further comprise treating each test sub-population with a test compound, wherein each test sub-population is treated with a different test compound. The test compound(s) may, for example, be obtained from a library. The library may comprise any collection of two or more test compounds that is believed to possibly contain one or more compounds that may cause DNA DSBs. Each sub-population may be treated with a different test compound such that the ability of each compound to cause DNA DSBs may be evaluated.

The method may further comprise contacting (i) a first portion of each treated test sub-population and (ii) a first portion of a control biological sample with an antibody or antigen binding fragment thereof that specifically binds to γ-H2AX and forms a first complex with the γ-H2AX; contacting (i) a second portion of each treated test sub-population and (ii) a second portion of a control biological sample with an antibody or antigen binding fragment thereof that specifically binds to an H2A core protein and forms a second complex with the H2A core protein; and contacting the first and second complexes of the control biological sample and the treated test sub-populations with an antibody or antigen binding fragment thereof that specifically binds to H2AX and forms a third complex with H2AX in the first complex and forms a fourth complex with H2AX in the second complex. The antibody or antigen binding fragment thereof that specifically binds to γ-H2AX; the antibody or antigen binding fragment thereof that specifically binds to an H2A core protein; the antibody or antigen binding fragment thereof that specifically binds to H2AX; the first, second, third, and fourth complexes; and the contacting may be as described herein with respect to other aspects of the invention. The control biological sample may be identical to the test biological sample with the exception that the control biological sample has not been treated with a test compound.

The method may further comprise detecting the third and fourth complexes in the control biological sample and the treated test sub-populations; quantifying the third and fourth complexes in the control biological sample and the treated test sub-populations; determining a ratio of the quantity of the third complex to the quantity of the fourth complex in the control biological sample; and determining a ratio of the quantity of the third complex to the quantity of the fourth complex in the treated test sub-populations. The detecting, quantifying, and determining of the ratio may be carried out as described herein with respect to other aspects of the invention.

The method may further comprise comparing the ratio of the quantity of the third complex to the quantity of the fourth complex in the control biological sample to the ratio of the quantity of the third complex to the quantity of the fourth complex in the treated test sub-populations, wherein an increase in the ratio in a treated test sub-population as compared to the ratio in the control biological sample indicates that the test compound has the ability to cause DNA DSBs. The comparing may be carried out as described herein with respect to other aspects of the invention.

Another embodiment of the invention provides a method of testing compounds for ability to cause DNA DSBs in a host. The method may comprise administering a test compound to the host and obtaining a biological sample from the host after the host has been administered the test compound. The host, the biological sample from the host, and the test compounds may be as described herein with respect to other aspects of the invention.

The method may further comprise contacting (i) a first portion of a control biological sample and (ii) a first portion of the host biological sample with an antibody or antigen binding fragment thereof that specifically binds to γ-H2AX and forms a first complex with the γ-H2AX; contacting (i) a second portion of the control biological sample and (ii) a second portion of the host biological sample with an antibody or antigen binding fragment thereof that specifically binds to an H2A core protein and forms a second complex with the H2A core protein, wherein the control biological sample has not been exposed to the test compound; and contacting the first and second complexes of the control biological sample and the host biological sample with an antibody or antigen binding fragment thereof that specifically binds to H2AX and forms a third complex with H2AX in the first complex and forms a fourth complex with H2AX in the second complex. The antibody or antigen binding fragment thereof that specifically binds to γ-H2AX; the antibody or antigen binding fragment thereof that specifically binds to an H2A core protein; the antibody or antigen binding fragment thereof that specifically binds to H2AX; the first, second, third, and fourth complexes; and the contacting may be as described herein with respect to other aspects of the invention. The control biological sample may be identical to the biological sample from the host except that the control biological sample has not been exposed to the test compound. For example, the control biological sample may be obtained from a host that has not been administered a test compound or from the host prior to administering a test compound.

The method may further comprise detecting the third and fourth complexes in the control biological sample and the host biological sample; quantifying the third and fourth complexes in the control biological sample and the host biological sample; determining a ratio of the quantity of the third complex to the quantity of the fourth complex in the control biological sample; and determining a ratio of the quantity of the third complex to the quantity of the fourth complex in the host biological sample. The detecting, quantifying, and determining of the ratio may be carried out as described herein with respect to other aspects of the invention.

The method may further comprise comparing the ratio of the quantity of the third complex to the quantity of the fourth complex in the control biological sample to the ratio of the quantity of the third complex to the quantity of the fourth complex in the host biological sample, wherein an increase in the ratio in the host biological sample as compared to the ratio in the control biological sample indicates that the test compound has the ability to cause DNA DSBs in the host. The comparing may be carried out as described herein with respect to other aspects of the invention.

The methods of screening test compounds for ability to cause DNA DSBs and the methods of testing compounds for ability to cause DNA DSBs in a host may provide many advantages. For example, the methods may be useful for identifying and developing new drugs that cause DNA DSBs, which may be useful for treating any of a variety of different diseases, e.g., cancer. The methods may be useful for testing any one or more of (1) whether alterations of a drug increase the drug's effectiveness for inducing DNA DSBs; (2) the mechanism(s) of drug-induced DNA DSBs and/or drug-induced effects on DNA DSB repair; (3) which cancer types are targeted by a particular drug, (4) whether a drug targets a protein involved in DNA DSB repair, (5) whether a drug targets a cancer associated with a mutated gene, e.g., a gene involved in DNA DSB repair, and (6) the effect of different combinations of drugs on DNA DSB repair. The methods of testing compounds for ability to cause DNA DSBs in a host may be useful for determining whether a drug candidate causes DNA DSBs in tumor-bearing animals and/or cancer patients in clinical trials.

Any of the inventive methods described herein may further comprise forming any of the complexes described herein in the presence of one or more protamines. The one or more protamines may, advantageously, reduce non-specific binding and/or increase the signal-to-background ratio.

The following examples further illustrate the invention but, of course, should not be construed as in any way limiting its scope.

Example 1

This example demonstrates the performance of the γ-H2AX immunoassay.

Materials:
Anti-γ-H2AX (Ser139) mouse monoclonal antibody, clone JBW301 (1 µg/µL) Lot # DAM1567248 (Millipore). Used at 1:250 dilution.
Anti-histone H2AX rabbit polyclonal antibody (1.7 µg/µL) Lot #778559 (Abeam). Used at 1:850 dilution.

Goat anti-rabbit horseradish peroxidase (HRP)-conjugated polyclonal antibody Lot #101008. Used at 1:1000 dilution.

γ-H2AX peptide standard, lyophilized powder (custom preparation from Invitrogen (Waltham, Mass.), synthetic peptide: AVLLPKKTSATVGPKAPSGGK-KATQASQEY), wherein the serine at position 27 is phosphorylated (SEQ ID NO: 2).

Pierce REACTI-BIND plates (96-well) (Thermo Scientific) were coated with anti-7-H2AX antibody (Millipore) diluted to a concentration of 4 μg/mL in 0.1 M pH 9.6 carbonate buffer (Sigma-Aldrich, St. Louis, Mo.), 100 μL/well, for 2 hours at 37° C. The γ-H2AX synthetic peptide standard or a whole-cell extract was added to each well and incubated for antigen capture overnight at 4° C. Plates were incubated with 100 μL/well of 2 μg/mL anti-histone H2AX rabbit polyclonal antibody (Abcam) diluted in 2% bovine serum albumin (BSA)/phosphate buffered saline (PBS) supplemented with 1 μL/mL mouse serum for 2 hours (h) at 24° C. Subsequently, 100 μL/well HRP-conjugated affinity-purified goat anti-rabbit (KPL) was added at a final concentration of 1 μg/mL diluted in 2% BSA/PBS, supplemented with 1 μL/mL mouse serum, and incubated for 1 hour at 24° C. Finally, 100 μL/well of freshly prepared SUPERSIGNAL ELISA Pico chemiluminescent substrate (Thermo Scientific, Waltham, Mass.) was added to the plate and immediately read on a TECAN INFINITE M200 plate reader (Tecan Group Ltr., Maennedorf, Switzerland). A standard curve was generated by plotting the RLU (relative light unit) values that were obtained for a range of concentrations of the γ-H2AX standard peptide (FIG. 1A). The average γ-H2AX concentration for each cell extract was then determined using the standard curve (FIG. 1B).

Example 2

This example demonstrates the performance of the total H2AX immunoassay.

Materials:
anti-H2A core protein HIST1H2AC monoclonal antibody, 4F10 (Novus, Cat #: H00008334-M01), Lot # D8231-4F10. Used at 1:250 dilution.
anti-histone H2AX rabbit polyclonal antibody (Abcam, Cat #: ab10475), Lot #778559. Used at 1:850 dilution.
Goat anti-rabbit HRP-conjugated polyclonal antibody (KPL, Cat #: 074-15-061), Lot #120504. Used at 1:1000 dilution.
Total H2AX recombinant standard, lyophilized powder (Axxora, Cat #: ALX-201-176-M005), Lot # L16677. Used standard stock concentration at 33000 pM.

Figures 2A, 2B:
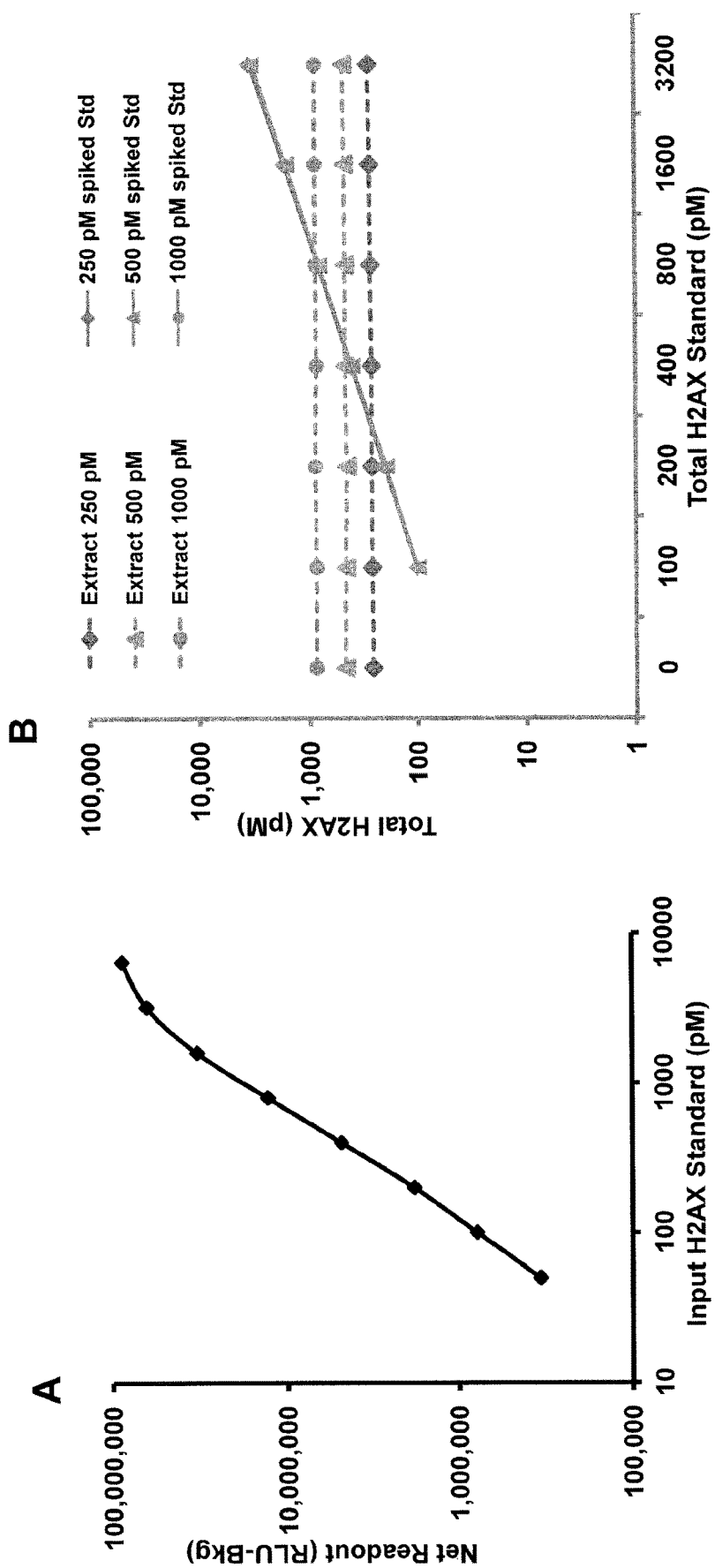
FIG. 2A is a graph (standard curve) showing the net readout (RLU-Bkg) detecting various concentrations of H2AX (pM) using chemiluminescent ELISA. Samples contained the standard H2AX protein at zero, 50, 100, 200, 400, 800, 1600, 3200 and 6400 pM. The background (Bkg) with zero pM standard is about 500,000 RLU.
FIG. 2B is a graph showing the independence of standard curve values on sample composition. A well-characterized and quantified extract was diluted to 250 pM (diamonds), 500 pM (triangles), or 1000 pM (circles) H2AX. Aliquots of each dilution were spiked with amounts of the standard H2AX protein peptide to zero, 100, 200, 400, 800, 1600 and 3200 pM. After the assay, the readouts were converted to H2AX protein concentrations. Solid lines represent measured values of H2AX protein concentrations after subtraction of input extract concentrations. Dashed lines represent measured values of extract concentrations of H2AX after subtraction of input standard concentrations.

Pierce REACTI-BIND plates (96-well) were coated with total anti-H2A core protein HIST1H2AC monoclonal antibody (Novus, St. Charles, Mo.) diluted to a concentration of 4 μg/mL in 0.1 M pH 9.6 carbonate buffer (Sigma-Aldrich), 100 μL/well, for 2 hours at 37° C. A total H2AX recombinant standard or whole-cell extract (250 pM, 500 pM, or 1,000 pM) was added to each well and incubated for antigen capture overnight at 4° C. Plates were incubated with 100 pt/well of 2 μg/mL total anti-histone H2AX rabbit polyclonal antibody (Abcam) diluted in 2% BSA/PBS supplemented with 1 μL/mL mouse serum for 2 h at 25° C. Subsequently, 100 pt/well HRP-conjugated affinity-purified goat anti-rabbit (KPL, Inc., Gaithersburg, Md.) was added at a final concentration of 1 μg/mL diluted in 2% BSA/PBS, supplemented with 1 μL/mL mouse serum, and incubated for 1 hour at 25° C. Protamines were added to decrease non-specific binding and to increase the signal to background ratio. Finally, 100 μL/well of freshly prepared SUPERSIGNAL ELISA Pico chemiluminescent substrate (Thermo Scientific) was added to the plate and immediately read on a TECAN INFINITE M200 plate reader. A standard curve was generated by plotting the RLU values that were obtained for a range of concentrations of the H2AX standard peptide (FIG. 2A). The average total H2AX concentration for each cell extract was then determined using the standard curve (FIG. 2B).

Example 3

This example demonstrates the parameters and controls of the assays of Examples 1 and 2.

Inter-assay precision was measured by running three replicates of (a) a total H2AX standard and assay controls, as described in Example 2 (Table 1) and (b) a γ-H2AX standard and assay controls, as described in Example 1 (Table 2). All three runs for the total H2AX immunoassay passed the inter-assay acceptance criteria (% coefficient of variation (CV)<25%) with a range from 6 to 21% for the standards and 2.2 to 7.3% for the controls. All three runs for the γ-H2AX immunoassay passed the inter-assay acceptance criteria (% CV<25%) with a range from 1-12%. The results in Tables 1 and 2 are summarized in Table 3.

TABLE 1

| H2AX Standard (pM) | Average RLU (n = 3) | Standard Deviation (SD) | % CV |
|---|---|---|---|
| 50 | 865,720 | 184,054 | 21 |
| 100 | 1,063,562 | 168,332 | 16 |
| 200 | 1,418,546 | 218,046 | 15 |
| 400 | 2,298,028 | 327,995 | 14 |
| 800 | 4,611161 | 370,373 | 8 |
| 1600 | 10,482,498 | 851,476 | 8 |
| 3200 | 26,055,096 | 1,696,172 | 7 |
| 6400 | 59,158,022 | 3,389,425 | 6 |

| Assay Control | Average pM (n = 3) | SD | % CV |
|---|---|---|---|
| Low Control | 216.1 | 15.8 | 7.3 |
| Medium Control | 844.8 | 49.3 | 5.8 |
| High Control | 2337.0 | 51.0 | 2.2 |

TABLE 2

| γH2AX Standard pM | Average RLU (n = 3) | SD | % CV |
|---|---|---|---|
| 5 | 992,667 | 122,261 | 12 |
| 10 | 2,016,850 | 134,112 | 7 |
| 20 | 4,598,600 | 277,146 | 6 |
| 40 | 10,021,317 | 467,893 | 5 |
| 80 | 20,811,817 | 1,459,080 | 7 |
| 160 | 37,371,983 | 930,881 | 2 |
| 320 | 58,789,817 | 2,240,098 | 4 |
| 640 | 79,191,483 | 1,063,448 | 1 |

| Assay Control | Average pM (n = 3) | SD | % CV |
|---|---|---|---|
| Low Control | 79.9 | 1.5 | 1.9 |
| Medium Control | 221.5 | 7.6 | 3.4 |
| High Control | 558.3 | 33.4 | 6.0 |

TABLE 3

| Assay | γH2AX assay | Total H2AX assay |
|---|---|---|
| Dynamic Range | 5-640 pM | 50-6400 pM |
| Linearity | 99.8% | 95.4% |
| Low Control | 60-90 pM | 154-275 pM |
| Mid Control | 150-300 pM | 602-1004 pM |
| High Control | 400-640 pM | 2075-2844 pM |

Readout ranges were prepared for the lot of tumor cell lines to be used as controls (C) during development of the total H2AX assay (Table 4) and the γ-H2AX assay (Table 5). For γ-H2AX, the Low-C sample contained un-irradiated MCF7 cells while the High-C sample contained MCF7 cells that were irradiated at 10 Gy and frozen 30 minutes later. Extracts of both were prepared at 1E7 cells/mL and diluted 1:3. The Mid-C sample was a mixture containing 70% Low-C and 30% High-C.

For total H2AX, the Low-C sample contained un-irradiated MCF7 cells diluted 1:200 from a stock extract of 1E7 cells/mL while the Mid-C sample contained MCF7 cells diluted 1:50 from the same stock extract. The High-C sample contained SN12C cell extract diluted 1:50 from a stock of 1E7 cells/mL.

TABLE 4

| Tumor Lysate Control (C) Level | Example Range of RLUs | Example Acceptable Readout Value (pM) |
|---|---|---|
| Low-C | 9.3E5-1.8E6 | 154-275 |
| Mid-C | 2.9E6-5.6E6 | 602-1004 |
| High-C | 1.3E7-2.0E7 | 2075-2844 |

TABLE 5

| Tumor Lysate Control Level | Example Range of RLUs | Example Acceptable Readout Value (pM) |
|---|---|---|
| Low-C | 5.9E6-7.7E6 | 53-82 |
| Mid-C | 1.0E7-2.2E7 | 181-228 |
| High-C | 2.2E7-5.1E7 | 458-583 |

Example 4

This example demonstrates the preclinical testing of the γ-H2AX immunoassay of Example 1.

Human breast cancer cell lines HCT 116 or MCF 7 (ATCC) were cultured with 10% fetal bovine serum at 37° C. in a 5% $CO_2$ incubator. The cells were treated with the topoisomerase I inhibitor topotecan, the apoptosis-inducing biomolecule tumor necrosis factor (TNF)-related apoptosis-inducing ligand (TRAIL), or IR. The γ-H2AX immunoassay (γ-H2AX ELISA) was compared with γ-H2AX detection by both Western blot and immunofluorescence assay (IFA).

The ELISA detected changes in γ-H2AX in HCT116 cell cultures induced by a variety of treatments in vitro and was overall highly correlated to both IFA and Western blot following treatment with topotecan or TRAIL (Table 6). With the less active treatment of IR, only a modest correlation between ELISA and Western blot was observed, but the high correlation with IFA remained.

TABLE 6

| Treatment | | ELISA (pM) | IFA (RLU) | Western Blot (RLU) |
|---|---|---|---|---|
| Topotecan (1 μM) | Control | 135 | 2.5 | 2.5 |
| | 0 hr | 124 | 0.7 | 4.7 |
| | 1 hr | 2536 | 23.0 | 8.1 |
| | 3 hr | 3134 | 43.9 | 6.9 |
| | 6 hr | 4793 | 51.2 | 14.3 |
| TRAIL (0.1 μg/mL) | 0 hr | 134 | 2.0 | 2.7 |
| | 1 hr | 2764 | 34.5 | 17.3 |
| | 3 hr | 9276 | 72.2 | 45.8 |
| | 6 hr | 7703 | 49.6 | 43.5 |
| Ionizing Radiation | Control | 124 | 1.3 | 2.5 |
| | 0.1 Gy | 122 | 2.2 | 2.8 |
| | 0.5 Gy | 156 | 2.4 | 4.2 |
| | 1.0 Gy | 155 | 4.3 | 4.1 |
| | 2.0 Gy | 161 | 7.9 | 5.2 |
| | 5.0 Gy | 283 | 13.2 | 4.3 |

Example 5

This example demonstrates a method of determining the ratio of γ-H2AX to total H2AX in cancer cells treated with IR or topotecan.

Figures 6A, 6B, 6C:
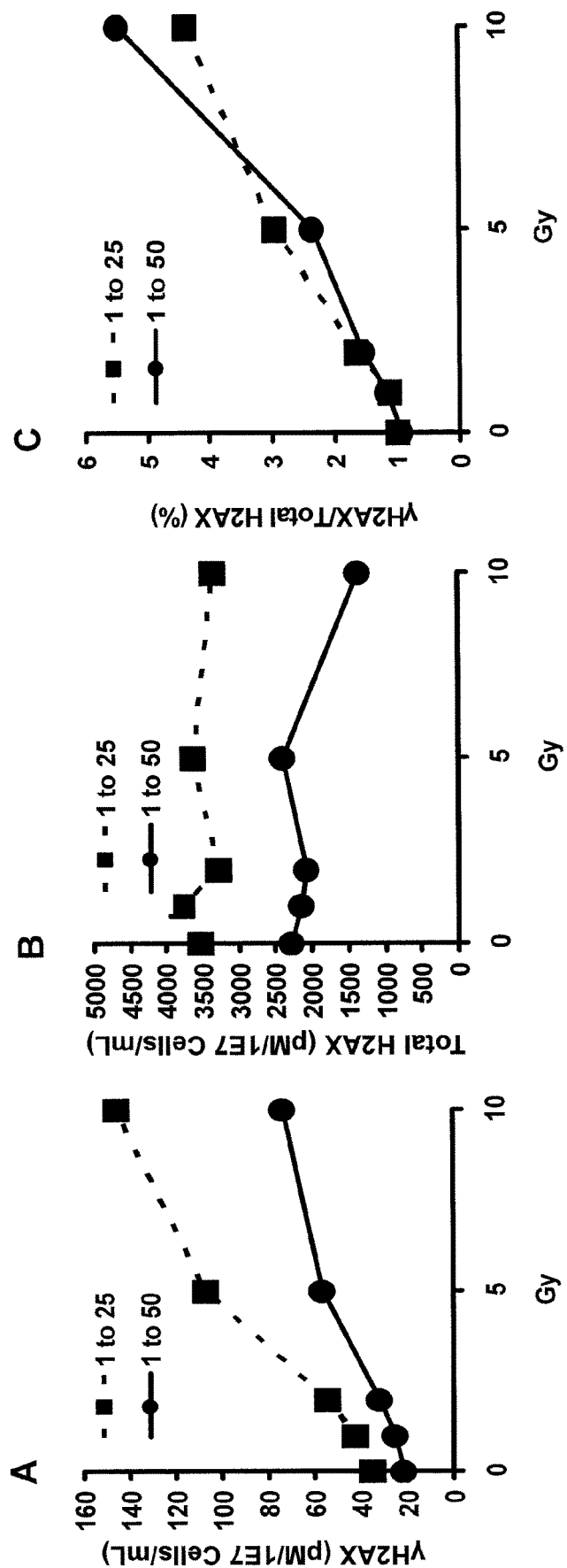
FIGS. 6A-6C are graphs showing γ-H2AX (pM) (A), H2AX (pM) (B), and γ-H2AX/Total H2AX (%) (C) values measured at two different dilutions of extract from 1E7 cells/mL THP1 cells, 1 to 25 (dashed line) and 1 to 50 (solid line).

THP1 leukemia cells were treated with the various amounts of IR shown in FIGS. 6A-6C. Extracts at $1\times10^7$ cells/mL were prepared of each irradiated sample, and two dilutions, 1 to 25 (30,000 cells/sample) and 1 to 50 (15,000 cells/sample) were used to measure γ-H2AX (FIG. 6A) and total H2AX (FIG. 6B) utilizing the γ-H2AX immunoassay of Example 1 and the total H2AX immunoassay of Example 2. FIGS. 6A-6C show data from the two dilutions (1:25 and 1:50). Using the values obtained in FIGS. 6A-6B, the ratio of γ-H2AX to total H2AX was calculated and is shown in FIG. 6C. As shown in FIG. 6C, the assay is independent of sample size.

The concentration of γ-H2AX in $1\times10^7$ HCT116 cells, MCF7 cells, or THP1 leukemia cells that had been treated with various doses of IR was measured using the γ-H2AX immunoassay of Example 1 (γ-H2AX ELISA). The results for THP1 are shown in FIG. 6A. As shown in FIG. 6A, the γ-H2AX ELISA functioned to determine the concentration of γ-H2AX in extracts of cancer cells treated with IR.

The concentration of total H2AX in the same extract used for the γH2AX determination was measured using the H2AX immunoassay of Example 2. The ratio of γ-H2AX to total H2AX was calculated for the HCT116 cells, MCF7 cells, and THP1 cells that had been treated with various doses of IR. The results for THP1 are shown in FIG. 6B. As shown in FIG. 6B, the γ-H2AX ELISA functioned to determine the concentration of γ-H2AX in extracts of cancer cells treated with IR.

Figures 3A, 3B:
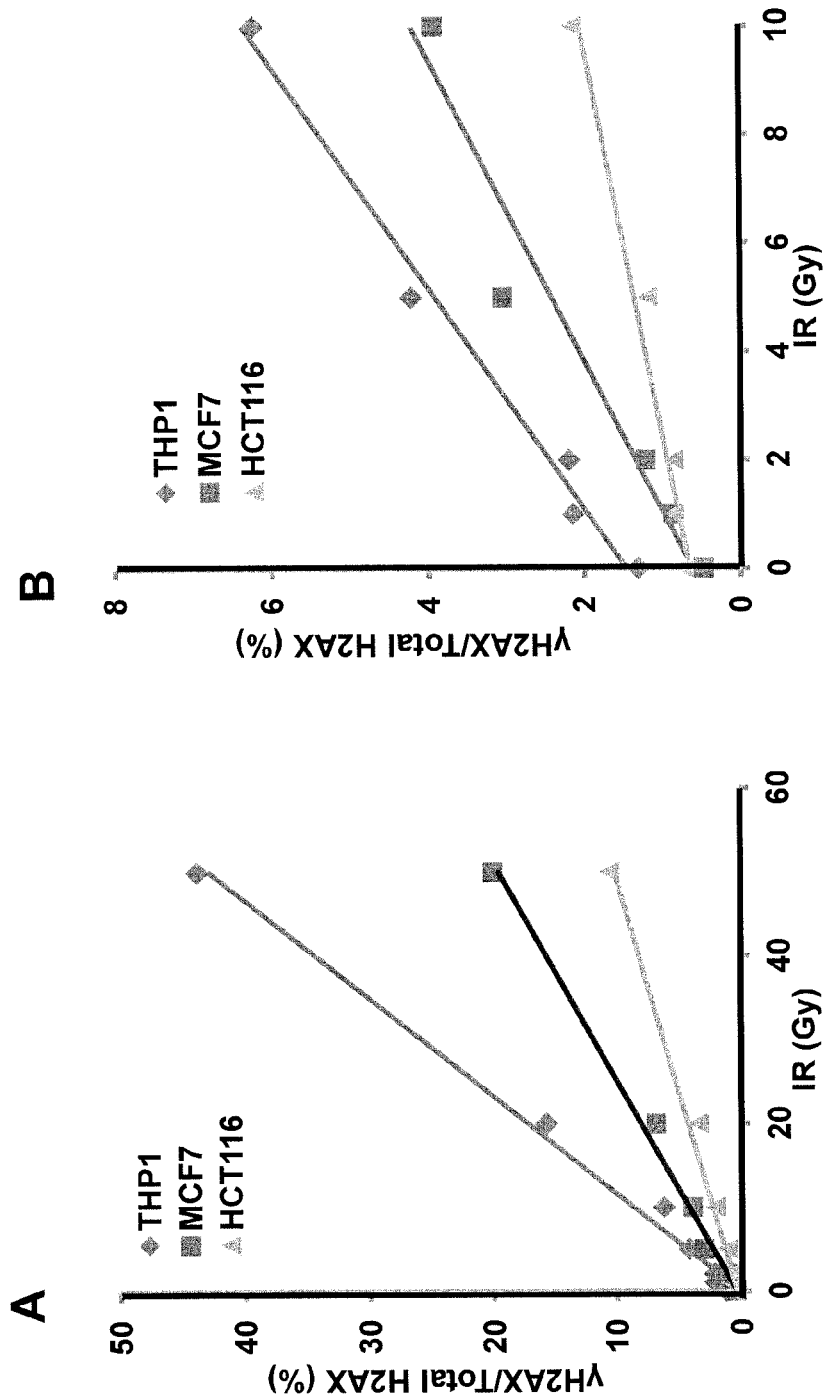
FIGS. 3A and 3B are graphs showing the ratio of γ-H2AX to total H2AX (%) detected in HCT116 cells (triangles), MCF7 cells (squares), or THP1 cells (diamonds) that had been treated with various doses of IR (Gy). The region below 10 Gy in FIG. 3A is expanded in FIG. 3B.

As shown in FIGS. 3A and 3B, the γ-H2AX and total H2AX immunoassays can be used to calculate the ratio of γ-H2AX to total H2AX in cells treated with IR. This value is approximately proportional to the number of DNA DSBs induced per nucleus and can be interpreted in terms of radiosensitivity of the various cell lines while γH2AX values alone cannot. FIG. 3B shows the region below 10 Gy, the region relevant to human exposures in radiological accidents and cancer treatment.

Figures 4A, 4B:
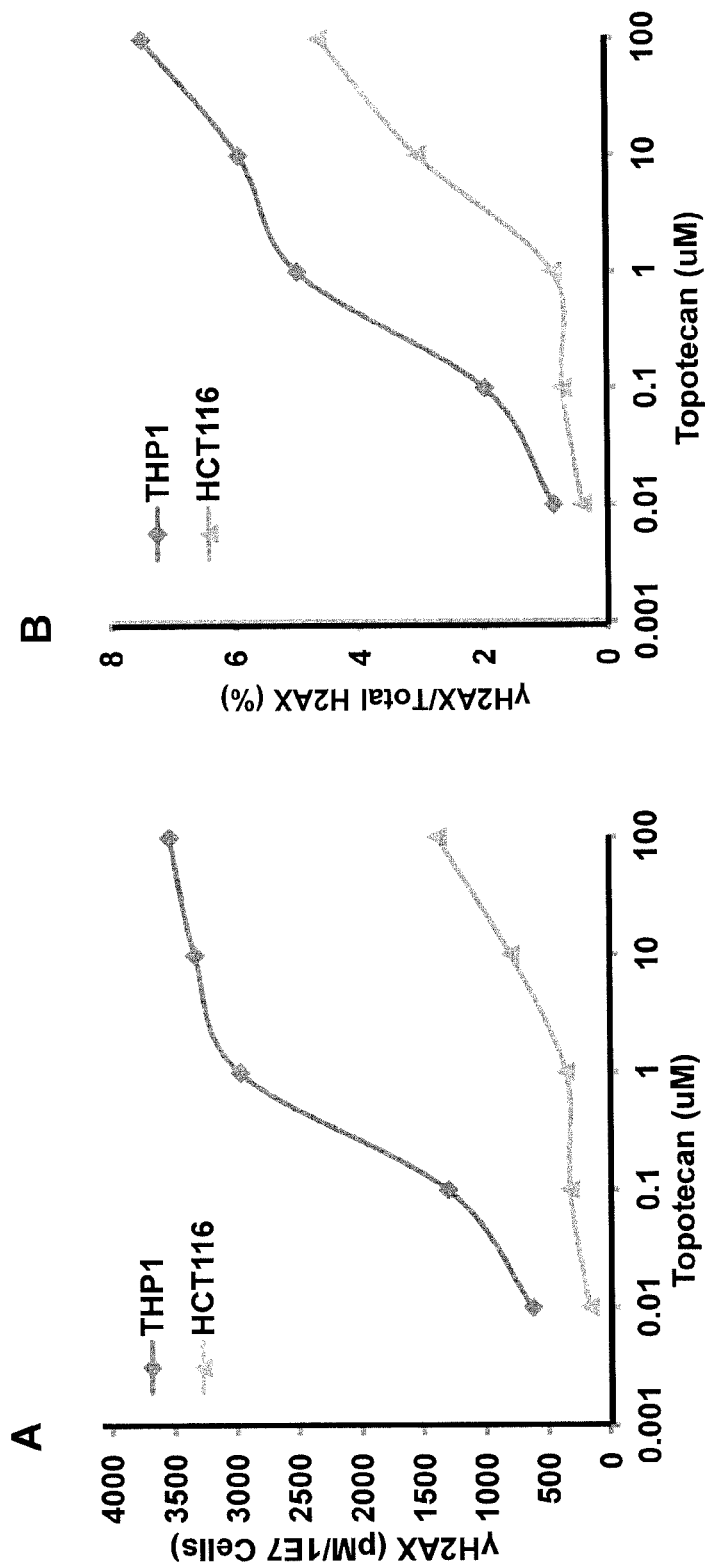
FIG. 4A is a graph showing the concentration of γ-H2AX (pM) detected per $1 \times 10^7$/mL of THP1 (diamonds) or HCT116 (triangles) cancer cells that had been treated with various concentrations of topotecan (μM).
FIG. 4B is a graph showing the percentage (%) of γ-H2AX per total H2AX in HCT116 cells (triangles) or THP1 cells (diamonds) that had been treated with various concentrations of topotecan (μM).

The concentration of γ-H2AX in extracts of HCT116 or THP1 cells that had been treated with various concentrations of topotecan was measured using the γ-H2AX ELISA. The results are shown in FIG. 4A. As shown in FIG. 4A, the γ-H2AX ELISA functioned to determine the concentration of γ-H2AX in $1\times10^7$ cancer cells treated with topotecan.

The concentration of total H2AX in 1×10⁷ HCT116 cells or THP1 cells that had been treated with various concentrations of topotecan was measured using the H2AX immunoassay of Example 2 (H2AX ELISA). The ratio of γ-H2AX to total H2AX was calculated for the HCT116 cells and THP1 cells that had been treated with various concentrations of topotecan. The results are shown in FIG. 4B. As shown in FIG. 4B, the γ-H2AX and total H2AX immunoassays can be used to calculate the ratio of γ-H2AX to total H2AX in cells treated with topotecan. This value more accurately reflects the relative effects of topotecan on different cell lines than γH2AX values alone.

Example 6

This example demonstrates a method of determining the ratio of γ-H2AX to total H2AX in various types of cancer cells and tumor panels.

Figure 5:
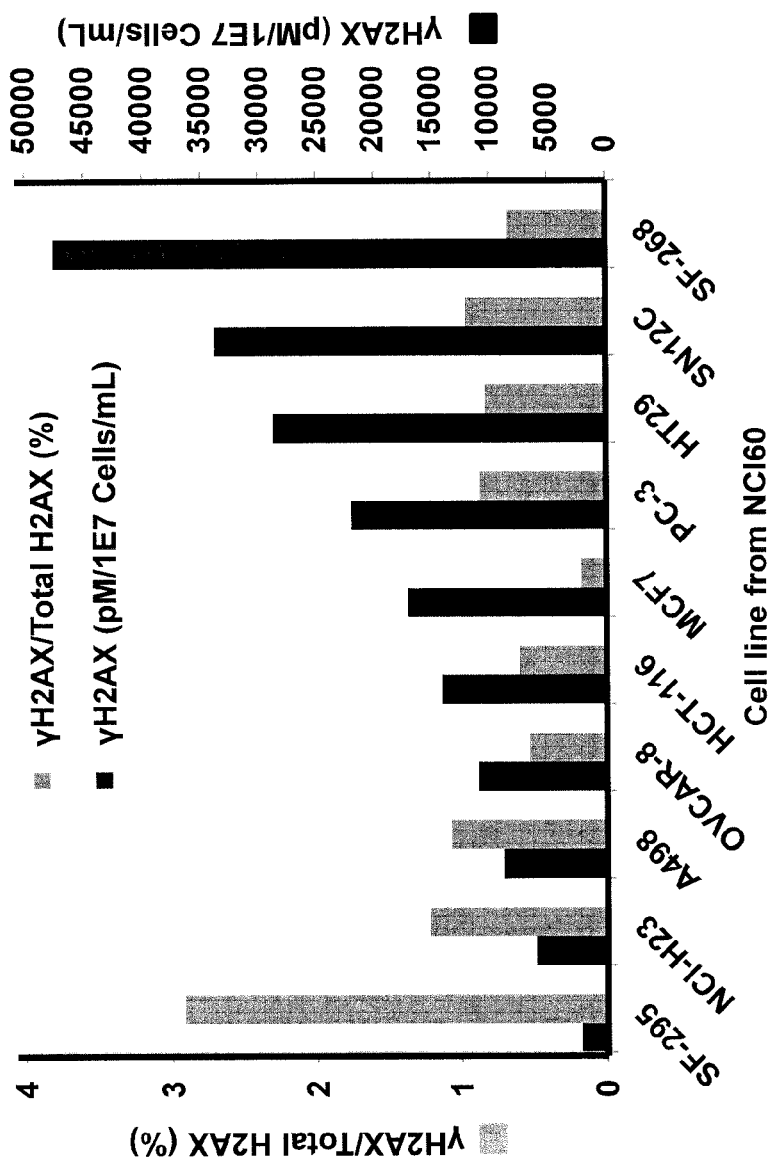
FIG. 5 is a graph comparing γ-H2AX (black bars) (γ-H2AX pM per 1E7 cells/mL) and γ-H2AX/Total H2AX (grey bars) (percentage (%) of γ-H2AX per total H2AX) for a selection of cell lines from the NCI60 tumor panel. Bars are arranged in increasing order of γ-H2AX value to demonstrate the effect of normalizing the γ-H2AX value to total H2AX.

The γ-H2AX immunoassay of Example 1 and the total H2AX immunoassay of Example 2 were used to determine the ratio of γ-H2AX to total H2AX in various cancer cell types (FIG. 5 and Table 7) and tumor panels (Table 8). The results are shown in FIG. 5 and Tables 7 and 8.

TABLE 7

| Cell Line | γH2AX (pM/1E7 Cells) | Total H2AX (pM/1E7 Cells) | γH2AX/Total H2AX (%) |
|---|---|---|---|
| NCI/ADR-RES Ovarian | 207 | 39631 | 0.52 |
| SF-268 CNS | 3837 | 461520 | 0.83 |
| SR Leukemia | 2921 | 56153 | 5.20 |
| HL-60 Leukemia | 1759 | 26993 | 6.52 |
| NCI60 Average +/− SD | 952 +/− 727 | 72026 +/− 62214 | 1.55 +/− 1.17 |

TABLE 8

| Tumor Panels | γH2AX/Total H2A X (%) | Standard Deviation (%) |
|---|---|---|
| CNS | 1.13 | 0.75 |
| Ovarian | 1.18 | 0.63 |
| Melanoma | 1.21 | 0.28 |
| NSCLC | 1.41 | 0.84 |
| Renal | 1.50 | 0.85 |
| Prostate | 1.51 | 0.21 |
| Breast | 1.67 | 1.39 |
| Colon | 1.76 | 1.25 |
| Leukemia | 2.86 | 2.48 |
| Average | 1.55 | 1.17 |

The γ-H2AX immunoassay of Example 1 and the total H2AX immunoassay of Example 2 were used to determine the ratio of basal concentrations of γ-H2AX to basal concentrations of total H2AX in a panel of 60 cancer cell lines (NCI 60), including six leukemia, nine non-small cell lung carcinoma, seven colon, six central nervous system, nine melanoma, seven ovarian, eight renal, two prostate, and six breast cancer cell lines. Assuming that all cell lines have 6×10⁹ base pairs of DNA and that all are in the G1 phase of the cell cycle (both of which are approximations), the H2AX as the maximum percentage of total H2A was calculated. The percentage values for H2AX out of total H2A generally agreed with those from other lines of research.

These data showed that the basal concentrations of γ-H2AX and total H2AX varied nearly 20 fold among the different cell types and were dependent on tumor type and cell line. The γ-H2AX/H2AX ratios ranged from 0.52% in an ovarian cell line (NC1/ADR-RES) to 6.52% in a leukemia cell-line (HL-60). Without being bound by a particular theory or mechanism, it is believed that the underlying cause of the variability may be linked to any one or more of chromosomal polyploidy, chromosomal amplification, genotypes and mutations related to DNA replication, and repair and cell cycle controls. It is also believed that unique patterns of γ-H2AX to total H2AX ratio changes due to treatment with IR or DNA-damaging drugs may reveal new targets for drug discovery and development.

Example 7

This example demonstrates that the assays of Examples 1 and 2 can be used to measure the amount of γ-H2AX induced by cancer drugs.

Figures 7A, 7B, 7C:
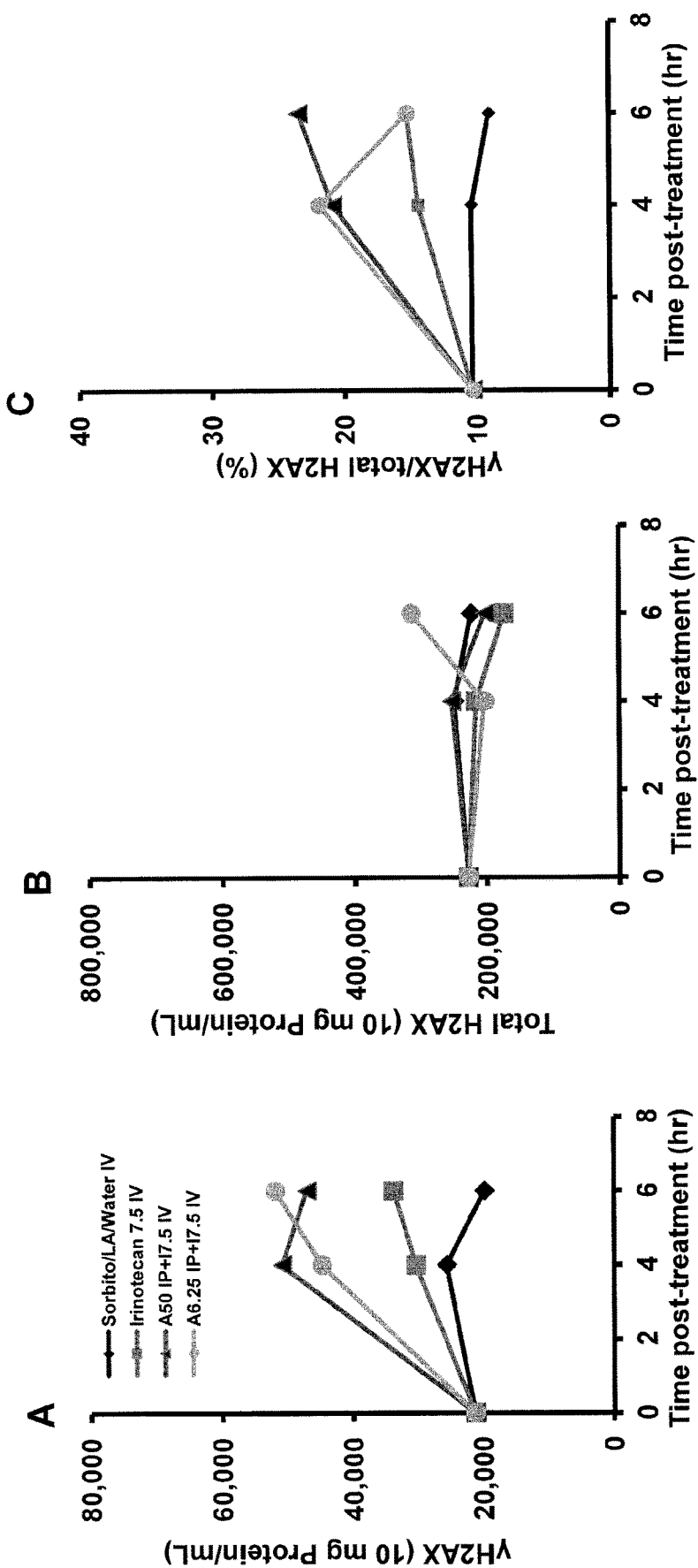
FIGS. 7A-7C are graphs showing the γ-H2AX (pM/10 mg protein/mL) (A), total H2AX (pM/10 mg protein/mL) (B) and γ-H2AX/Total H2AX (%) (C) values measured in biopsy samples from nude xenograft mice with human breast cancer tumors at various time points (hours) after administration of carrier (control) (diamonds), 7.5 units of irinotecan delivered intravenously (17.5 IV) alone (squares) or in combination with either 50 (triangles) or 6.25 (circles) units of AZD2281 delivered intraperitoneally (IP).

Nude mice containing tumors of the human breast carcinoma cell line MX1 were treated with various combinations of two cancer drugs, irinotecan and AZD2281. Irinotecan (7.5 units) was delivered intravenously (17.5 IV) alone or in combination with either 50 or 6.25 units of AZD2281 delivered intraperitoneally (IP). The control was the carrier for the drugs. At 6 hours post treatment, the tumors were biopsied. The biopsies were solubilized and prepared at 10 mg protein/mL. The solubilized, prepared biopsy samples were assayed for γ-H2AX (FIG. 7A) and total H2AX (FIG. 7B) at various time points after administration, and the respective ratios of γH2AX to total H2AX were calculated (FIG. 7C). As shown in FIG. 7C, irinotecan alone induced γ-H2AX modestly, while the combinations with AZD2281 induced substantially more γ-H2AX, particularly at 4 hours after administration.

Example 8

This example demonstrates that the assays of Examples 1 and 2 can be used to measure the amount of γ-H2AX in archived patient peripheral blood mononuclear cells (PB-MCs), bone marrow, and tumor biopsy samples.

Figures 8A, 8B, 8C, 8D, 8E, 8F:
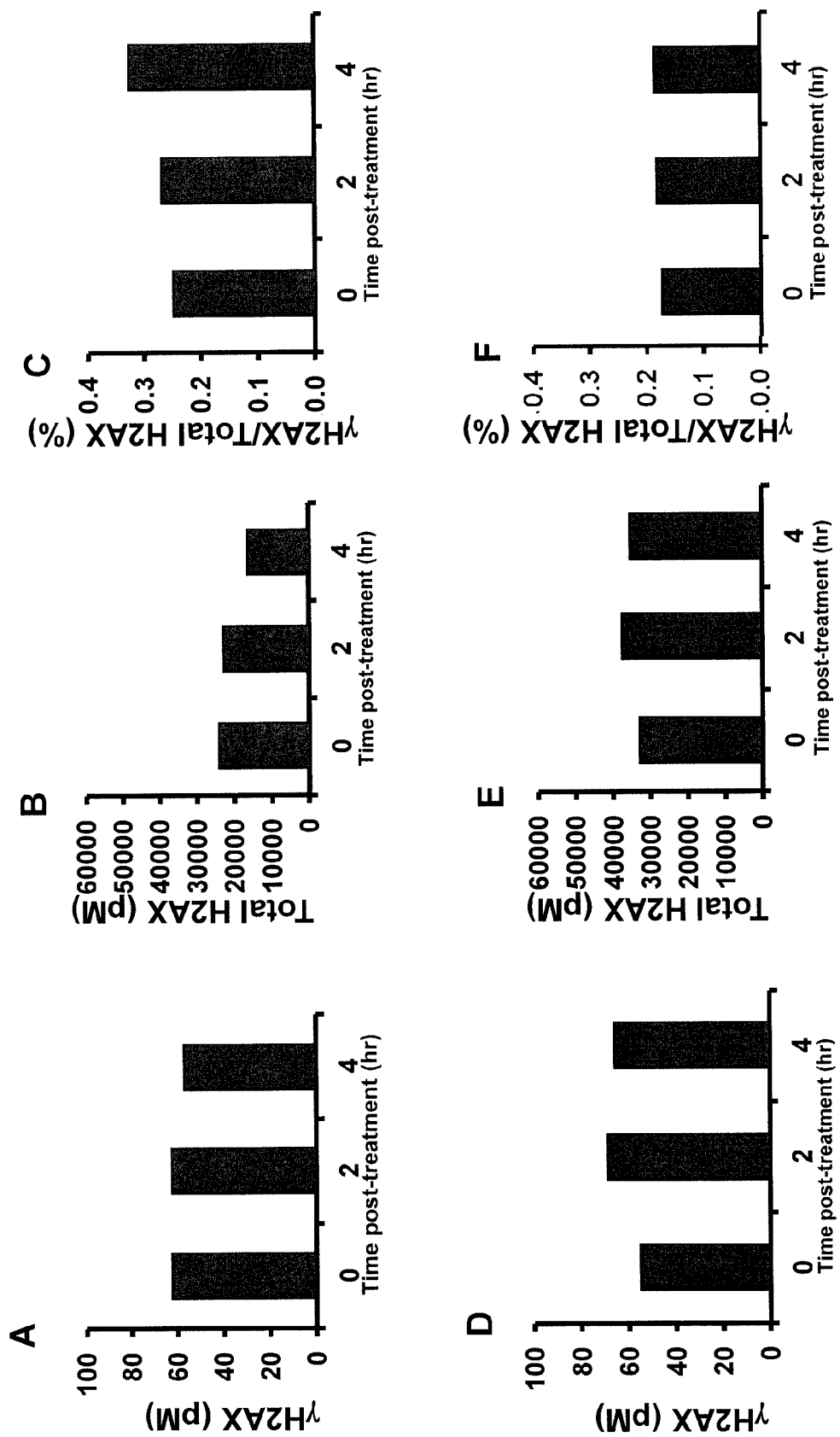
FIGS. 8A-8F are graphs showing the amounts of γ-H2AX (pM/1E7 cells/mL) (A and D) and total H2AX (pM/1E7 cells/mL) (B and E) and the ratio of γ-H2AX to total H2AX (%) (C and F) measured in peripheral blood mononuclear cells in archived blood samples from two patients (Patient A (A-C) and Patient B (D-F)) at various time points (hours) after drug administration.

Blood samples were taken from patients before treatment with drugs and at various time points after treatment. The blood samples were frozen and stored for later analysis. PBMCs from the stored samples were extracted and analyzed using the assays of Examples 1 and 2. The results are shown in FIGS. 8A-8C (Patient A) and FIGS. 8D-8F (Patient B). As shown in FIGS. 8C and 8F, Patient A had a modest increase in γ-H2AX levels, while patient B did not.

Figures 9A, 9B, 9C, 9D, 9E, 9F:
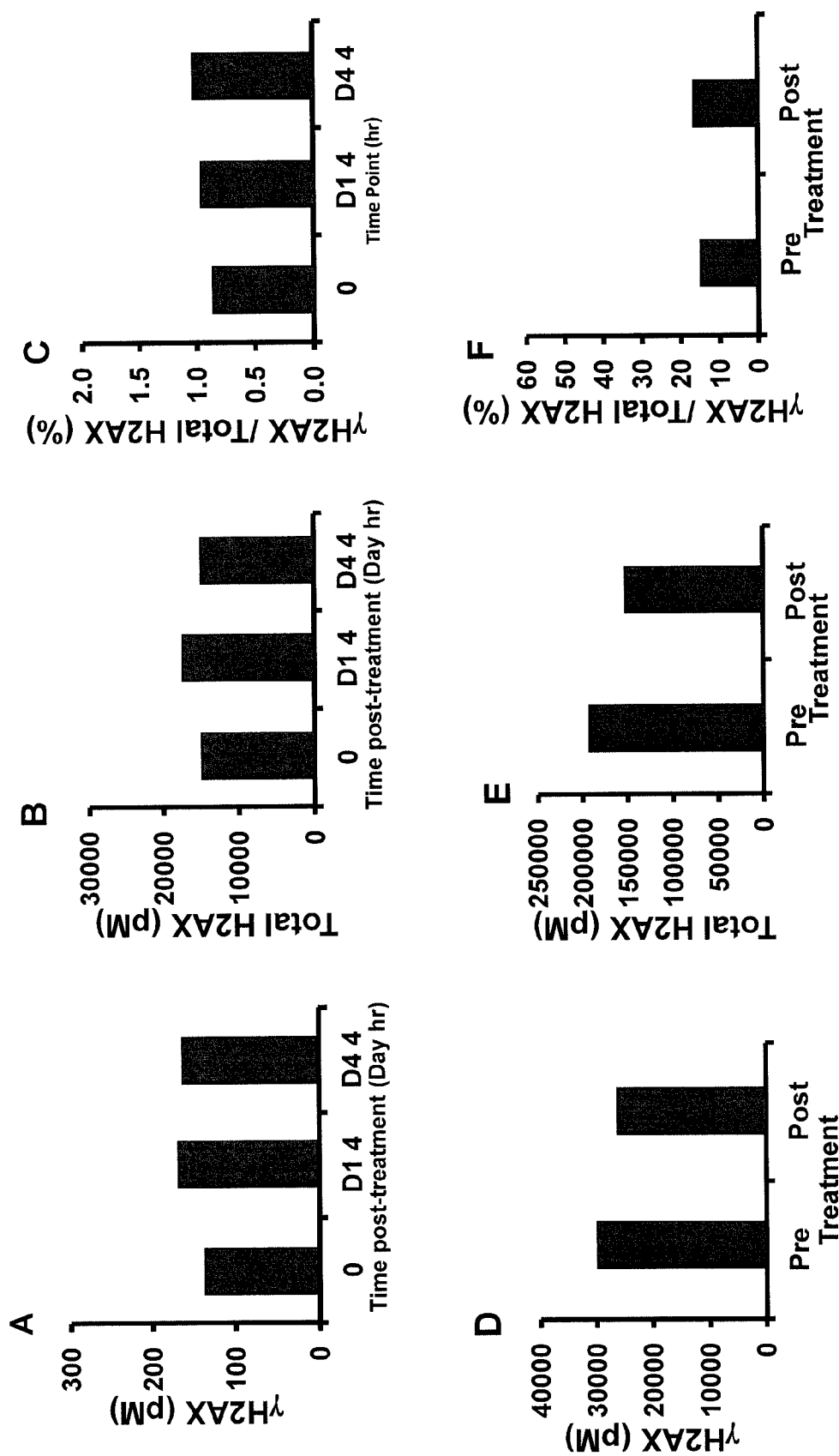
FIGS. 9A-9F are graphs showing the amounts of γ-H2AX (pM/1E7 cells/mL) (A and D) and total H2AX (pM/10 mg protein/mL) (B and E) and the ratio of γ-H2AX to total H2AX (%) (C and F) measured in archived patient bone marrow samples (A-C) and tumor biopsies (D-F) taken at various time points after drug administration.

Bone marrow and tumor biopsy samples were taken from patients before treatment with drugs and at various time points after treatment. The samples were frozen and stored for later analysis. Cells from the stored samples were extracted and analyzed by the assays of Examples 1 and 2. The results are shown in FIGS. 9A-9C (bone marrow) and FIGS. 9D-9F (tumor biopsy). As shown in FIGS. 9C and 9F, the assays of Examples 1 and 2 can be used to measure the amount of γ-H2AX in archived bone marrow and tumor biopsies.

The assays of Examples 1 and 2 were successfully used to measure the amount of γ-H2AX in the biospecimen types shown in Table 9.

TABLE 9

| Biospecimen Type | Number of Specimens |
| --- | --- |
| Tumor cell cultures | 136 |
| Mouse xenograft tumors | 144 |
| PBMCs | 18 |
| Bone marrow | 78 |
| Human tumor | 8 |

Example 9

This example demonstrates that the sensitivity of the combined assays of Examples 1 and 2 is approximately 0.2 Gy.

Figures 10A, 10B:
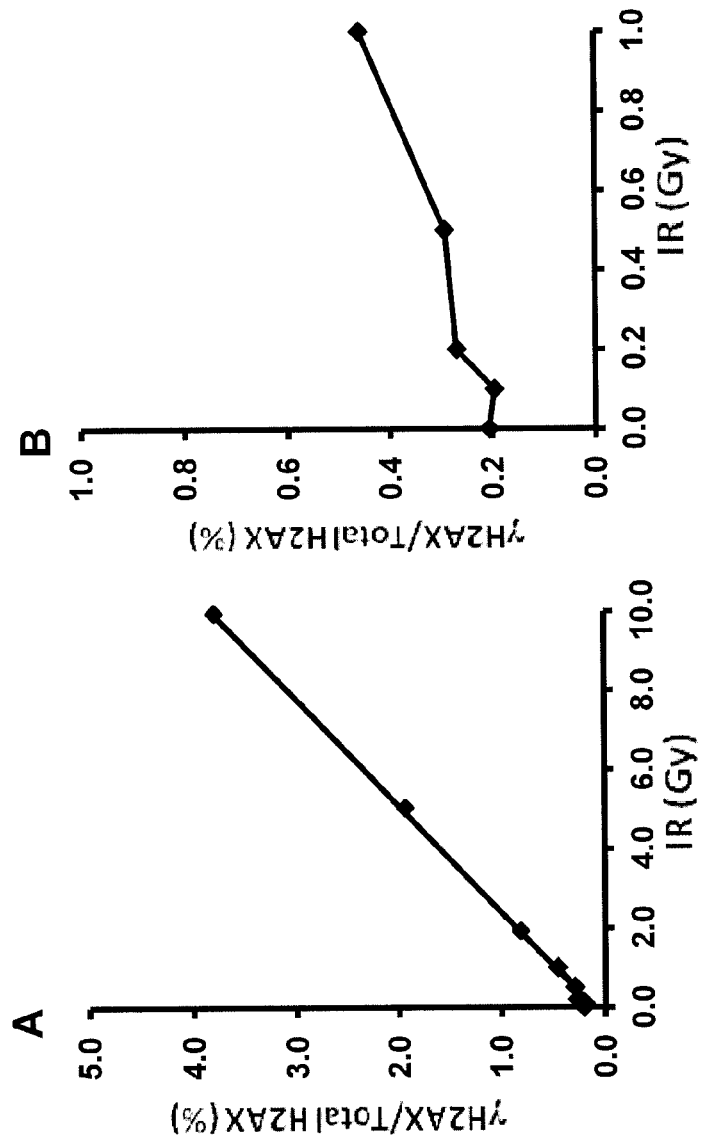
FIGS. 10A and 10B are graphs showing the ratio of γ-H2AX to total H2AX (%) detected in normal human fibroblasts that were exposed to various amounts of ionizing radiation (IR) (Gy). The region below 1 Gy in FIG. 10A is expanded in FIG. 10B.

Cultures of normal human fibroblasts (NHFs) were exposed to the amounts of radiation shown in FIG. 10A. The exposed cells were permitted to recover for 30 minutes, then analyzed for γ-H2AX and H2AX using the assays of Examples 1 and 2. The ratio of γ-H2AX to total H2AX was calculated, and the results are shown in FIGS. 10A and 10B. As shown in FIG. 10B, the sensitivity of the assay was approximately 0.2 Gy.

Example 10

This example demonstrates that the assays of Examples 1 and 2 may detect approximately 10,000 tumor cells in 0.25 mL of blood.

Figures 12A, 12B, 12C, 12D:
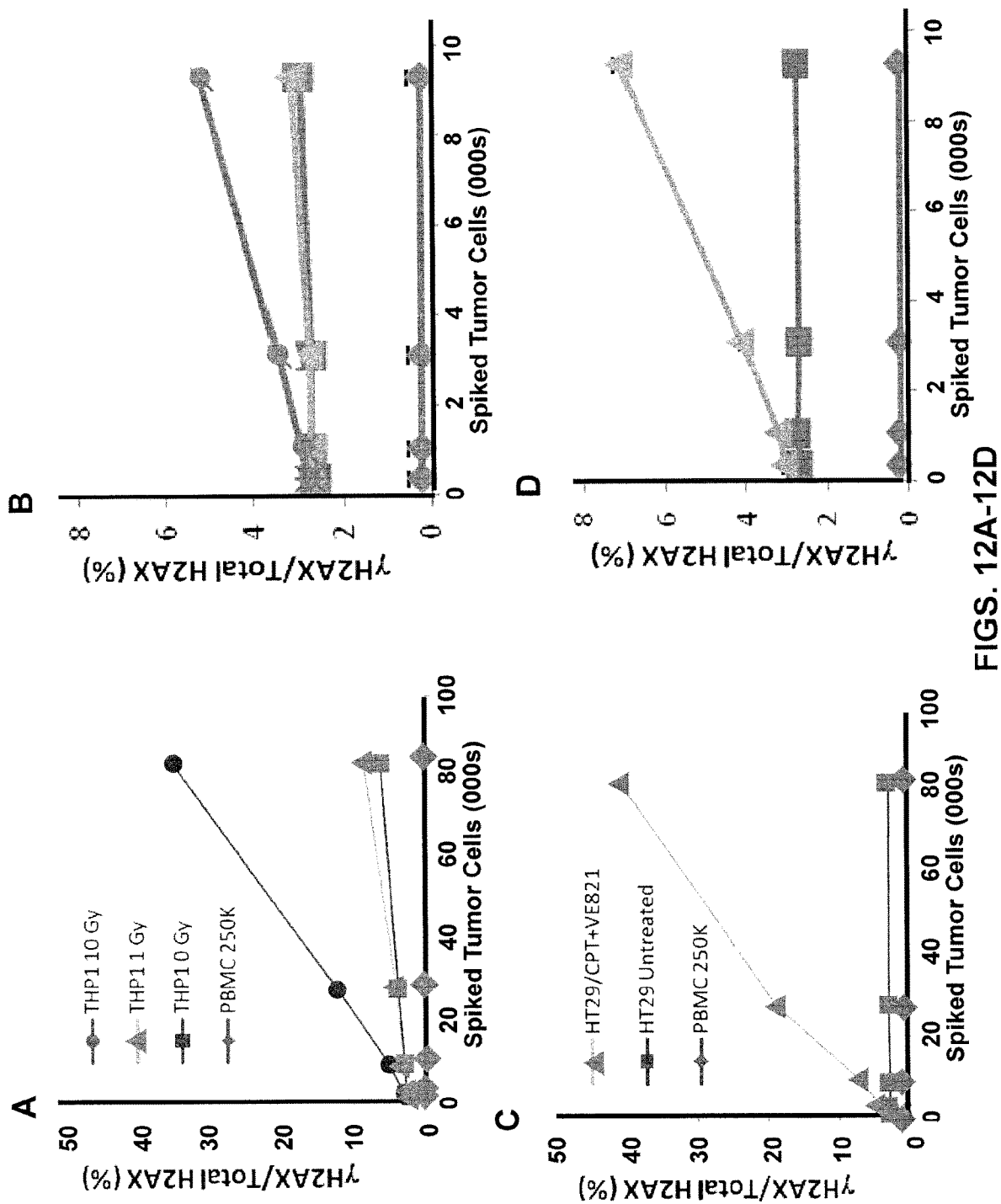
FIGS. 12A and 12B are graphs showing the percentage (%) of γ-H2AX per total H2AX detected in normal PBMC (diamonds) or PBMC that had been mixed with various numbers of THP1 tumor cells (spiked tumor cells) that had not been exposed to IR (squares) or tumor cells that had been exposed to 10 Gy (circles) or 1 Gy (triangles) of IR. The region below 10% γ-H2AX per total H2AX in FIG. 12A is expanded in FIG. 12B.
FIGS. 12C and 12D are graphs showing the percentage (%) of γ-H2AX per total H2AX detected in normal PBMC (diamonds) or PBMC that had been mixed with various numbers of HT29 tumor cells (spiked tumor cells) that were untreated (squares) or treated with ATR inhibitors VE-821 and camptothecin (CPT) (triangles). The region below 10% γ-H2AX per total H2AX in FIG. 12C is expanded in FIG. 12D.

Normal blood (250 μL) was left unmixed (PBMC) or mixed (spiked) with different numbers of THP1 tumor cells that had been treated with various doses of IR, then analyzed using the assays of Examples 1 and 2. The ratio of γ-H2AX to total H2AX was calculated, and the results are shown in FIGS. 12A and 12B. As shown in FIGS. 12A and 12B, approximately 10,000 tumor cells in 0.25 mL of blood could be detected.

Normal blood (250 μL) was unmixed or mixed (spiked) with different numbers of HT29 human colorectal adenocarcinoma tumor cells that were untreated or treated with ATR inhibitors VE-821 and camptothecin (CPT), then analyzed using the assays of Examples 1 and 2. The ratio of γ-H2AX to total H2AX was calculated, and the results are shown in FIGS. 12C and 12D. As shown in FIGS. 12C and 12D, approximately 10,000 tumor cells in 0.25 mL of blood could be detected.

Example 11

This example demonstrates that the immunoassays of Examples 1 and 2 may be used to detect the synergistic cytotoxicity of drug combinations using the ratio of γ-H2AX to total H2AX as readout for DNA DSB breaks.

Figure 11:
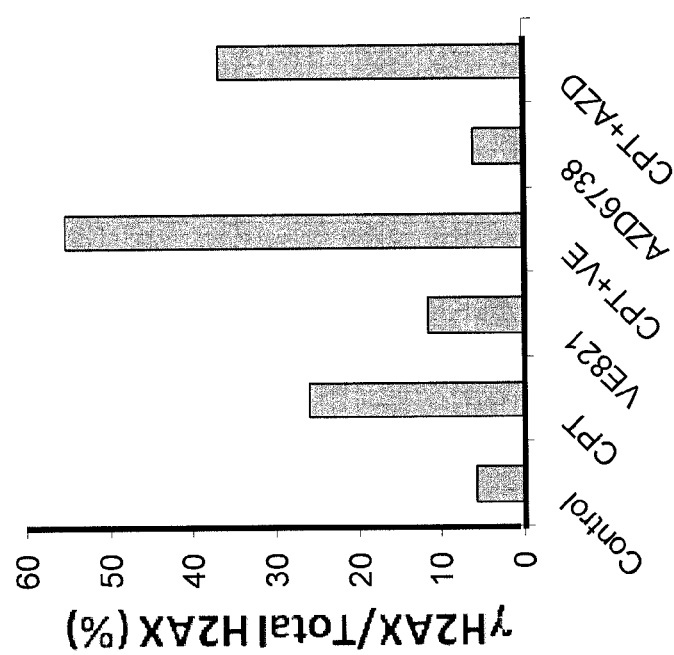
FIG. 11 is a graph showing the percentage (%) of γ-H2AX per total H2AX detected in untreated HT29 cells (control) or HT29 cells that were treated with single drugs (CPT, AZD6738 (AZD) or VE821 (VE)), or combinations of CPT plus AZD6738 or VE821.

Cultured HT29 cells were treated with a single drug (CPT, AZD6738 (AZD) or VE821 (VE)), or combination of CPT plus AZD6738 or VE821. For single drug treatment, CPT (1 μM) was added into the culture media for a one (1) hour treatment, then washed twice. Medium (without drug) was added, and the cells were cultured for an additional seven (7) hour culture. For AZD6738 or VE821 treatment, drug (1 μM) was added to the culture medium and the cells were cultured for a total of eight (8) hours without changing the media. For combination of CPT with ATR inhibitor treatment, HT29 was first treated with CPT at 1 μM for 1 hour, then washed twice. AZD6738 or VE821 was added at 1 μM, and the cells were cultured for an additional 7 hours. At the end of the eight (8) hour culture, the cells were harvested, extracted, and analyzed using the assays of Examples 1 and 2. The ratio of γ-H2AX to total H2AX was calculated, and the results are shown in FIG. 11. As shown in FIG. 11, the immunoassays of Examples 1 and 2 may be used to detect the synergistic cytotoxicity of drug combinations using the ratio of γ-H2AX to total H2AX as a readout for DNA DSB breaks.

Example 12

This example demonstrates that the immunoassays of Examples 1 and 2 detect DNA DSB in cells that have been treated with a genotoxic agent in vitro at a concentration as low as 1 nM.

Figure 13:
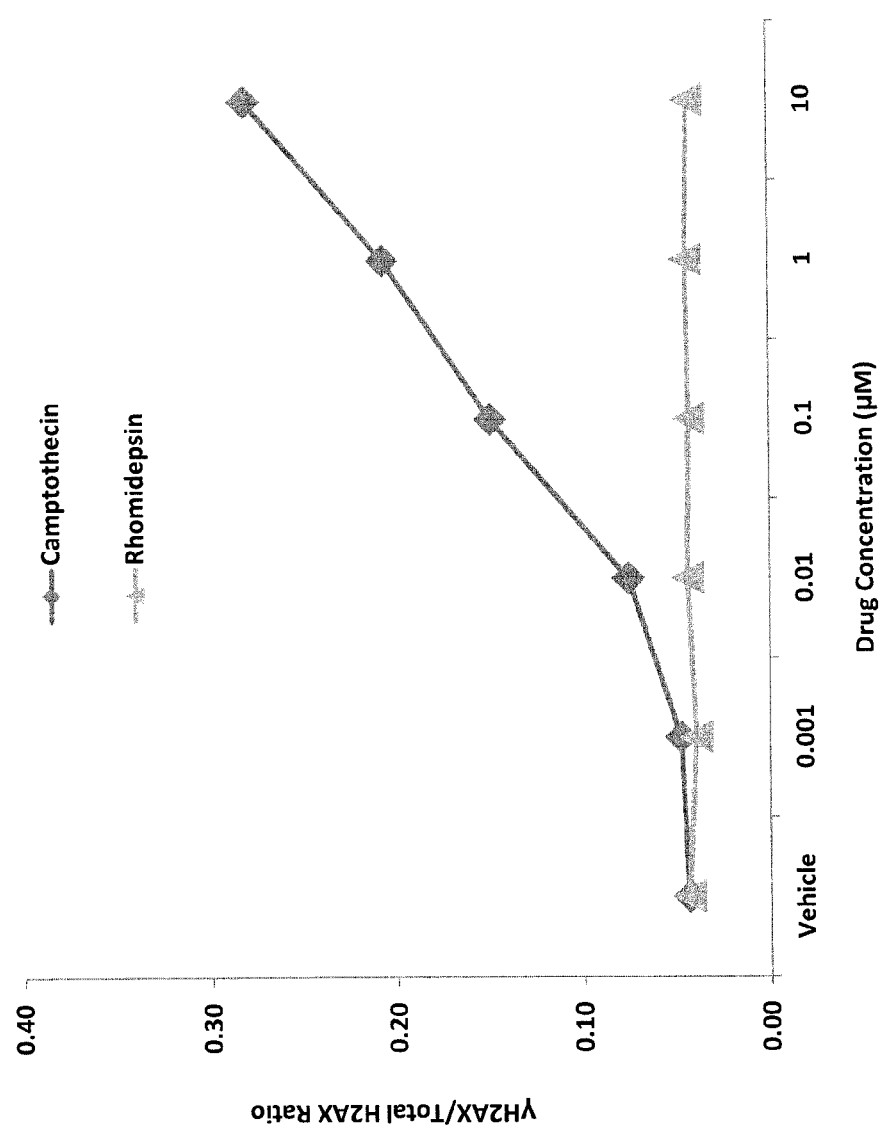
FIG. 13 is a graph showing the ratio of γ-H2AX to total H2AX measured in HT29 cells which were treated with the indicated concentrations of camptothecin (CPT) (diamonds) or rhomidepsin (triangles).

HT29 cells were treated with the genotoxic agent camptothecin (CPT) or the non-genotoxic agent rhomidepsin for 1 hour at a concentration of 0 (vehicle) 0.001, 0.001, 0.01, 1 or 10 μM. The cells were collected. The γ-H2AX immunoassay of Example 1 and the total H2AX immunoassay of Example 2 were used to determine the ratio of γ-H2AX to total H2AX in the collected cells. The results are shown in FIG. 13. DNA DSB, as measured by the ratio of γ-H2AX to total H2AX, was detected with CPT treatment as low as 1 nM. In contrast, no DNA DSB, as measured by the ratio of γ-H2AX to total H2AX, was detected following rhomidepsin treatment, even at a concentration as high as 10 μM.

Example 13

This example demonstrates that the γ-H2AX immunoassay of Example 1 and the total H2AX immunoassay of Example 2 provide a detectable signal of DNA DSB with as few as 160 cells when the cells are treated with a genotoxic agent at a concentration of 0.01 μM or higher in vitro.

Figure 14:
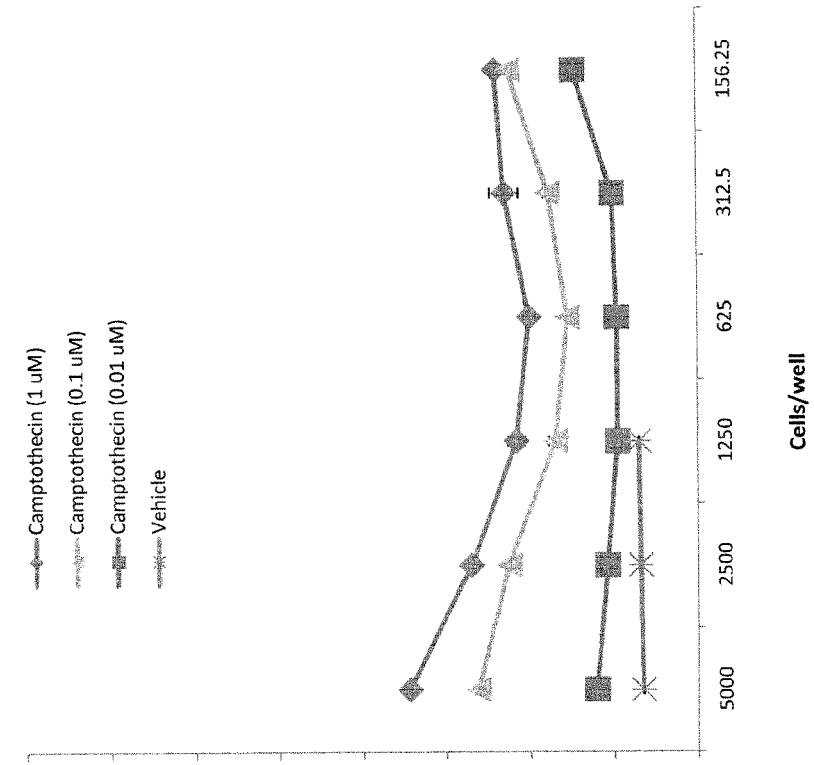
FIG. 14A is a graph showing the quantity of γ-H2AX (pM) measured in the indicated number of cells per well following treatment with CPT at a concentration of 0 μM (vehicle) (asterisks), 0.01 μM (squares), 0.1 μM (triangles) or 1 μM (diamonds).
FIG. 14B is a graph showing the quantity of total H2AX (pM) measured in the indicated number of cells per well following treatment with CPT at a concentration of 0 μM (vehicle) (asterisks), 0.01 μM (squares), 0.1 μM (triangles) or 1 μM (diamonds).
FIG. 14C is a graph showing the ratio of γ-H2AX to total H2AX measured in the indicated number of cells per well following treatment with CPT at a concentration of 0 μM (vehicle) (asterisks), 0.01 μM (squares), 0.1 μM (triangles) or 1 μM (diamonds).
Figure 14:
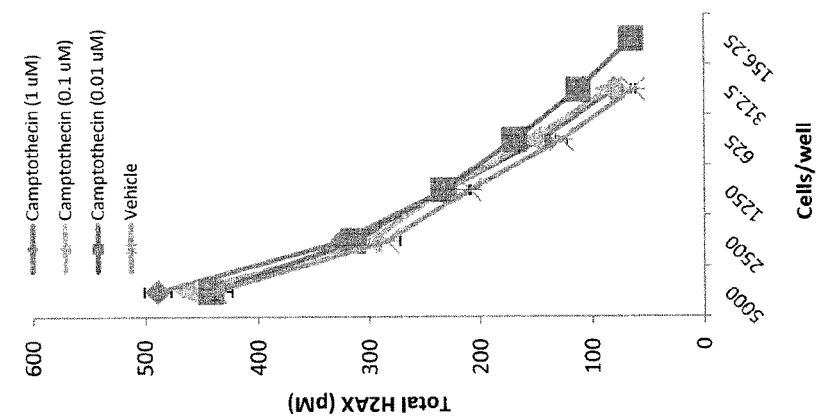
Figure 14:
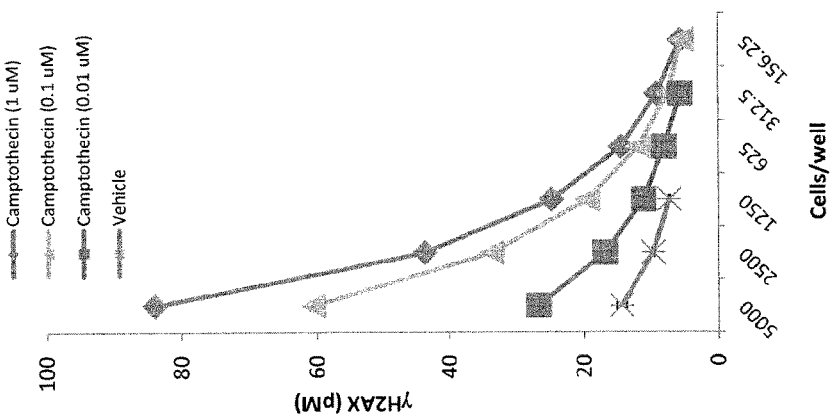

HT29 were treated with CPT for 1 hour at a concentration of 0 μM (vehicle), 0.01 μM, 0.1 μM or 1 μM. The cells were collected and further diluted to 5000, 2500, 1250, 625, 312, or 156 cells per assay. The γ-H2AX immunoassay of Example 1 was used to quantitate γ-H2AX (FIG. 14A) in the collected cells. The total H2AX immunoassay of Example 2 was used to quantitate total H2AX (FIG. 14B) in the collected cells. The ratio of γ-H2AX to total H2AX in the collected cells was determined (FIG. 14C). As shown in FIG. 14C, the ratio of γ-H2AX to total H2AX provided a detectable signal of DNA DSB with as few as 160 cells when the cells were treated with CPT at a concentration of 0.01 μM or higher.

Example 14

This example demonstrates that the immunoassays of Examples 1 and 2 detect DNA DSB in cells following treatment with a genotoxic agent in vitro.

The immunoassays of Examples 1 and 2 were tested for the ability to screen genotoxic agents. γ-H2AX is a sensitive and early signal of any one or more of DNA DSB, DNA repair, and apoptosis, any one or more of which may lead to tumor killing. Therefore, the immunoassays of Examples 1 and 2 were used for high throughput screening of potential agents for genotoxins and therapeutics. The genotoxic agents included Top1 inhibitors, Top2 inhibitors, DNA crosslink formers, and blockers of one or more of DNA replication, DNA repair, and the cell cycle, as shown in Table 10.

Figure 15:
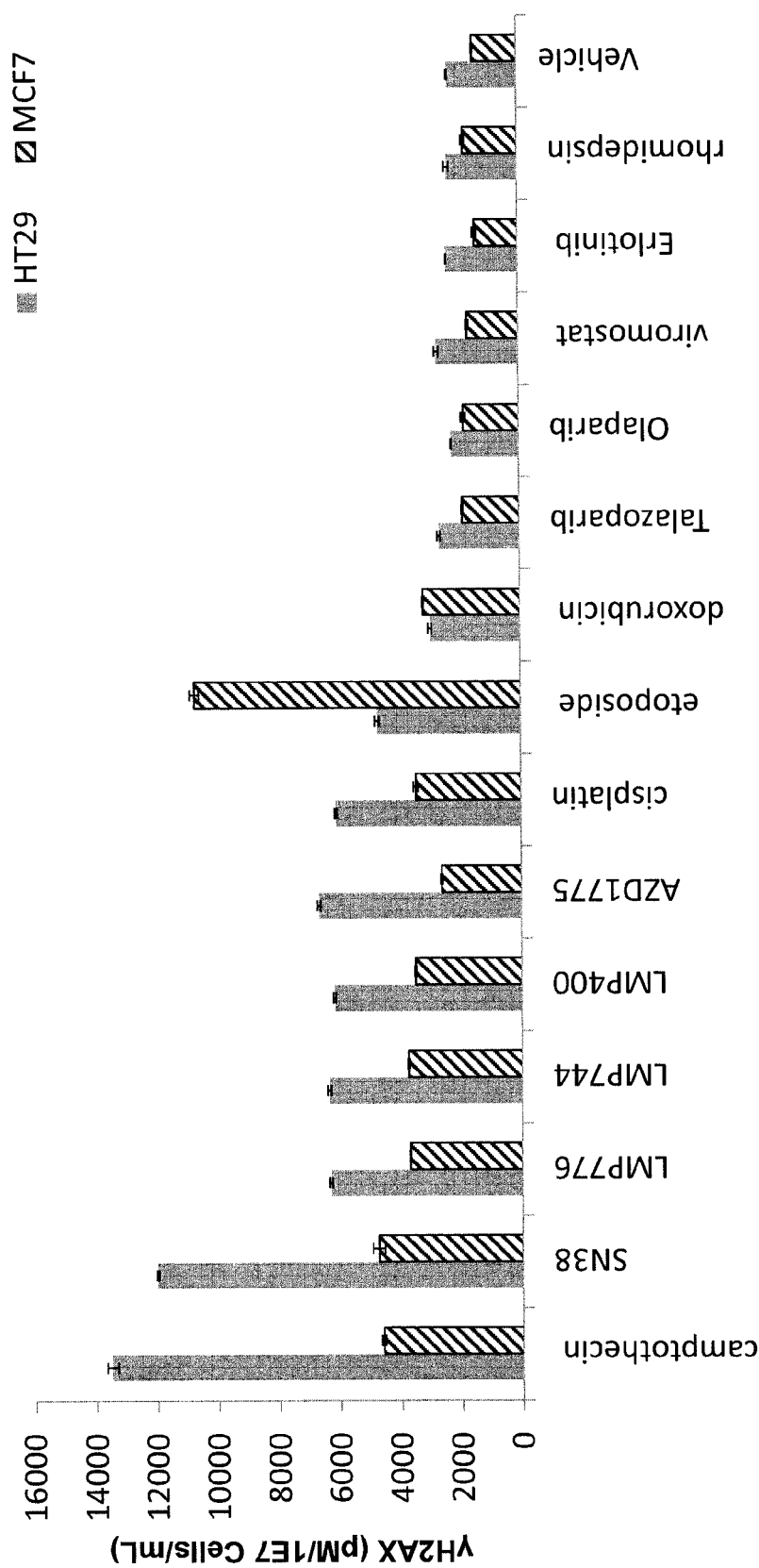
FIG. 15 is a graph showing the quantity of γ-H2AX per $1 \times 10^7$ HT29 cells/mL (grey bars) or $1 \times 10^7$ MCF7 cells/mL (striped bars) treated with vehicle (control) or the drug CPT, SN38, LMP776, LMP744, LMP400, AZD1775, cisplatin, etoposide, doxorubicin, talazoparib, olaparib, viromostat, erlotinib, or rhomidepsin.
Figure 16:
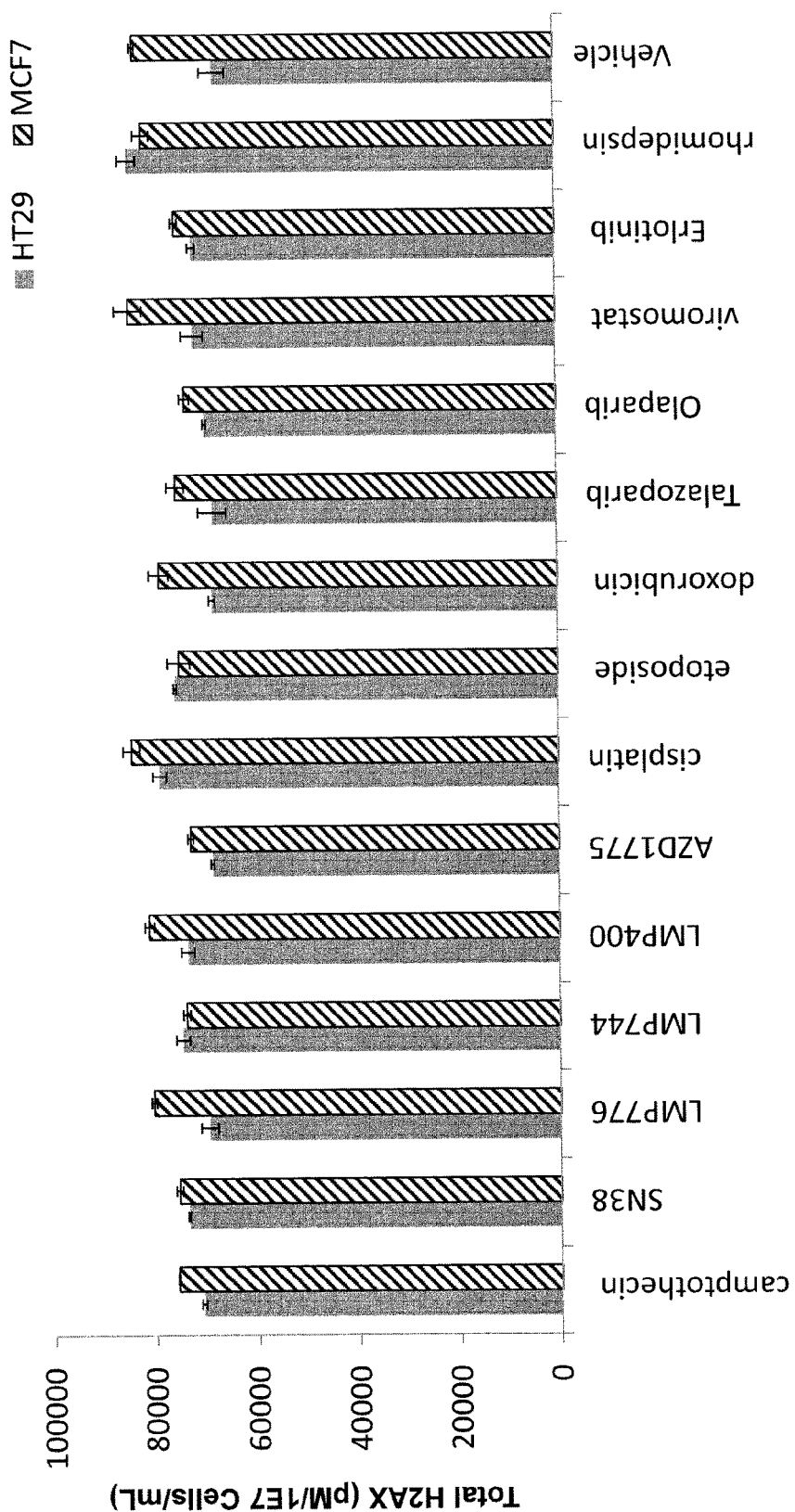
FIG. 16 is a graph showing the quantity of total H2AX per $1 \times 10^7$ HT29 cells/mL (grey bars) or $1 \times 10^7$ MCF7 cells/mL (striped bars) treated with vehicle (control) or the drug CPT, SN38, LMP776, LMP744, LMP400, AZD1775, cisplatin, etoposide, doxorubicin, talazoparib, olaparib, viromostat, erlotinib, or rhomidepsin.
Figure 17:
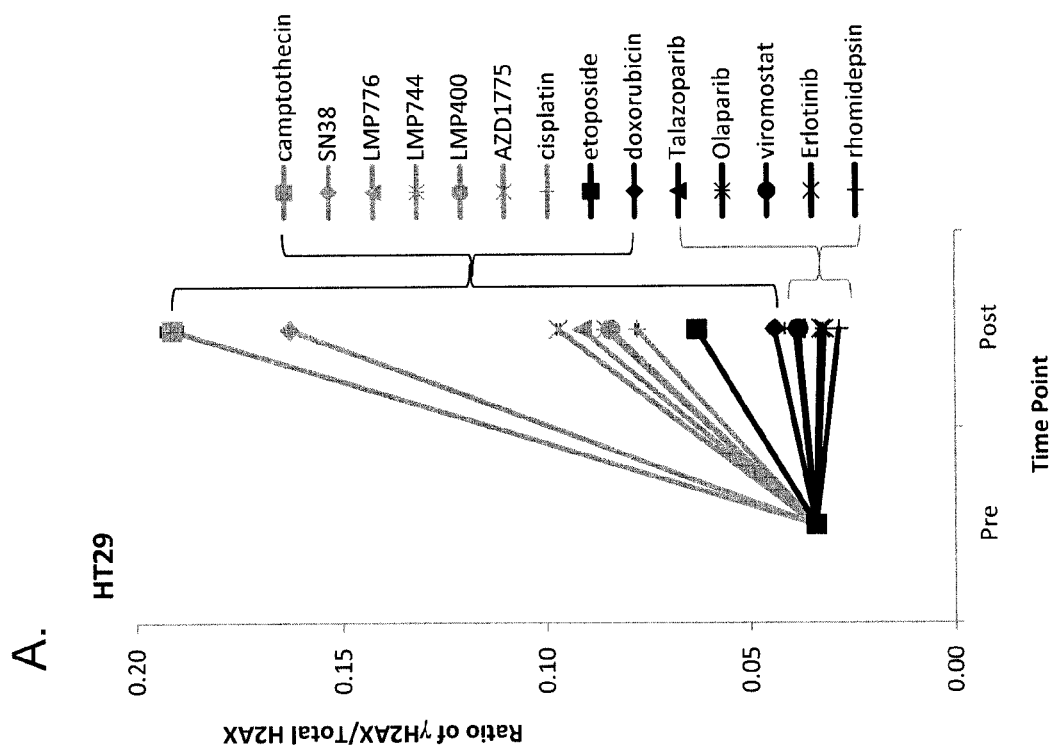
FIGS. 17A and 17B are graphs showing the ratio of γ-H2AX to total H2AX measured in HT29 cells (A) or MCF7 cells before (Pre) or after (Post) treatment with camptothecin (grey squares), SN38 (grey diamonds), LMP776 (grey triangles), LMP744 (grey asterisks), LMP400 (grey circles), AZD1775 (grey X), cisplatin (grey +), etoposide (black squares), doxorubicin (black diamonds), talazoparib (black triangles), olaparib (black asterisks), viromostat (black circles), erlotinib (black X), or rhomidepsin (black +).
Figure 17:
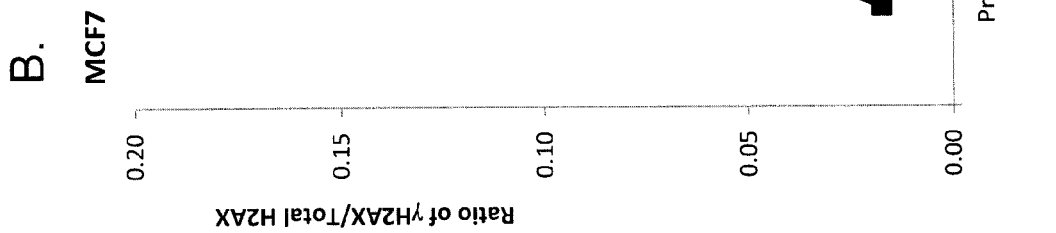

HT29 or MCF7 cells were plated overnight and separately treated with vehicle (control) or the drug CPT, SN38, LMP776, LMP744, LMP400, AZD1775, cisplatin, etoposide, doxorubicin, talazoparib, olaparib, viromostat, erlotinib, or rhomidepsin under the conditions shown in Table 10. Table 10 also indicates whether each drug is a genotoxic agent ("yes"), a non-genotoxic agent ("no"), or whether it is unknown whether the drug is a genotoxic agent ("?"). The γ-H2AX immunoassay of Example 1 was used to quantitate γ-H2AX (FIG. 15) per 1×10$^7$ collected cells. The total H2AX immunoassay of Example 2 was used to quantitate total H2AX (FIG. 16) per 1×10$^7$ collected cells. The ratio of γ-H2AX to total H2AX in the HT29 cells (FIG. 17A) and the MCF7 cells (FIG. 17B) was determined. As shown in FIGS. 17A and 17B, DNA DSB, as measured by the ratio of γ-H2AX to total H2AX, was detected with genotoxic agent treatment. In contrast, no DNA DSB, as measured by the ratio of γ-H2AX to total H2AX, was detected following non-genotoxic agent treatment.

TABLE 10

| Agent Name | Conc (μM) | Treatment Time (hr) | Genotoxic | Target |
|---|---|---|---|---|
| camptothecin | 10 | 1 | Yes | Top1 trapping |
| SN38 | 1 | 1 | Yes | Top1 trapping |
| LMP776 | 10 | 1 | Yes | Top1 trapping |
| LMP744 | 10 | 1 | Yes | Top1 trapping |
| LMP400 | 10 | 1 | Yes | Top1 trapping |
| etoposide | 100 | 1 | Yes | Top2 trapping |
| doxorubicin | 1 | 1 | Yes | Top2 trapping |
| cisplatin | 100 | 6 | Yes | Crosslinks |
| AZD1775 | 1 | 1 | Yes | Wee1 |
| Talazoparib | 1 | 1 | ? | PARP trapping |
| Olaparib | 1 | 1 | ? | PARP trapping |
| rhomidepsin | 1 | 1 | ? | HDAC |
| viromostat | 1 | 1 | No | tubulin |
| Erlotinib | 1 | 1 | No | EGFR |
| Vehicle | NA | 1 | No | NA |

NA = not applicable.

Example 15

This example compares the detection of DNA DSB using a microscope immunofluorescence assay (IFA) to the detection of DNA DSB using the immunoassays (IA) of Examples 1 and 2.

The presence of γ-H2AX in the cells treated as described in Example 14 was confirmed by staining using a labeled anti-γ-H2AX antibody and observing the intensity of the staining through a microscope. No staining was observed in the cells treated with vehicle. Staining was observed in the cells treated with, for example, 10 nM, 100 nM, 1 μM, and 10 μM CPT. The staining intensity increased as the concentration of CPT used to treat the cells increased.

Figure 18:
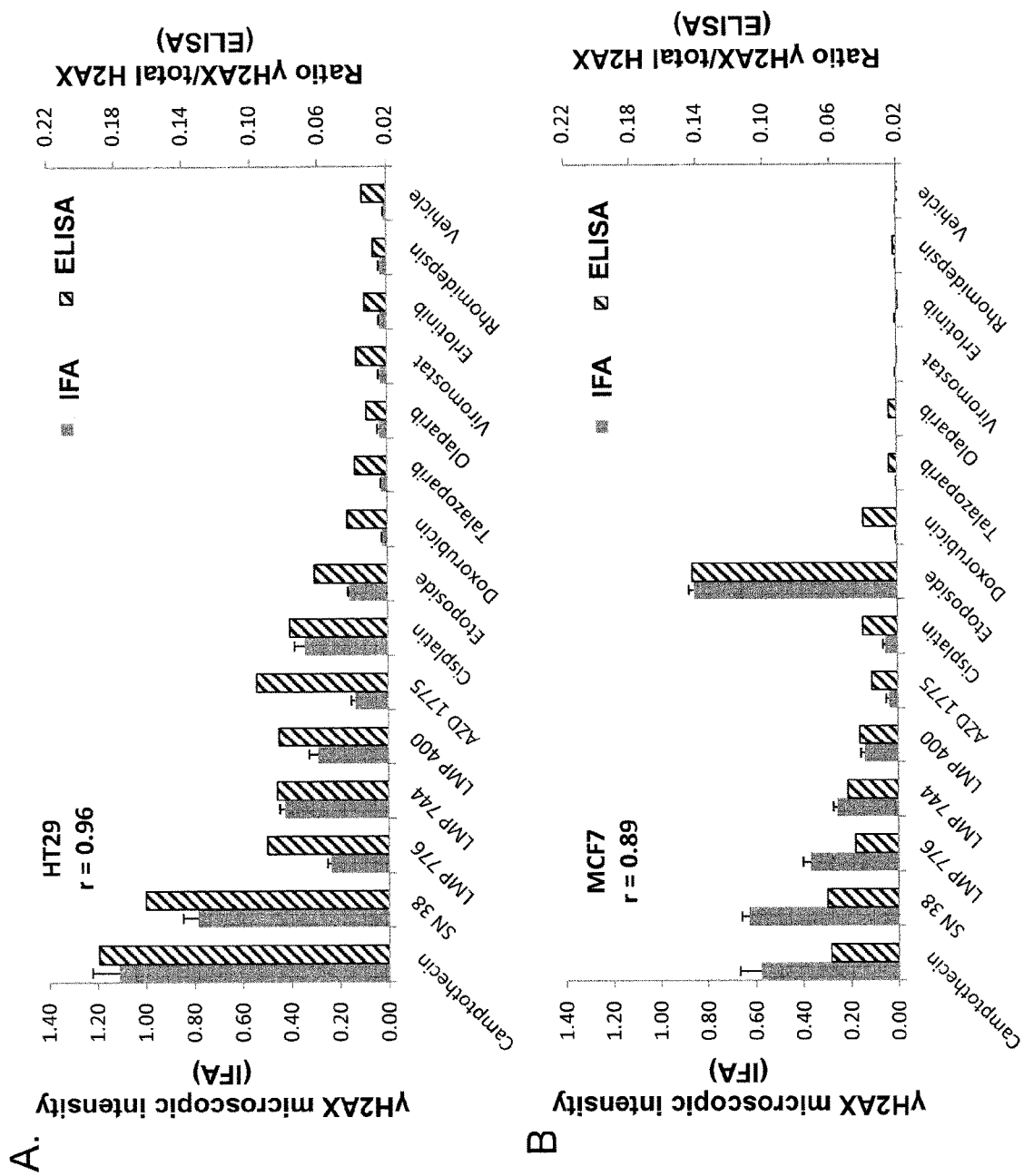
FIGS. 18A and 18B are graphs showing the intensity of staining for γ-H2AX using an anti-γ-H2AX antibody (microscope immunofluorescence assay (IFA)) (shaded bars) and the ratio of γ-H2AX to total H2AX (ELISA immunoassay (IA)) (striped bars) measured in HT29 cells (A) or MCF7 cells (B).

The γ-H2AX in the cells treated as described in Example 14 was quantified by staining using a labeled anti-γ-H2AX antibody and measuring the intensity of the staining, observed through a microscope (immunofluorescence microscope assay (IFA)). The quantity of γ-H2AX measured by staining intensity was compared to the ratio of γ-H2AX to total H2AX measured by the immunoassays (IA) of Examples 1 and 2. The results are shown in FIG. 18A (HT29) and FIG. 18B (MCF7).

Example 16

This example demonstrates that the immunoassays of Examples 1 and 2 can be used to detect DNA DSB induced by the treatment of cells in vitro with drugs.

Figure 19:
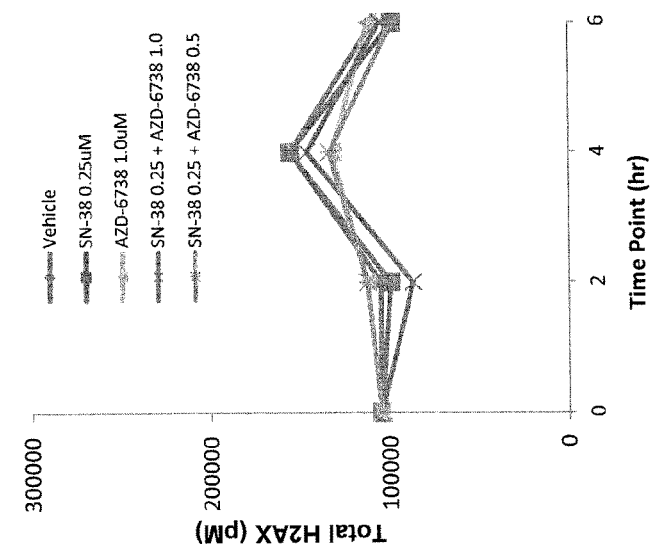
FIGS. 19A-19C are graphs showing the ratio of γ-H2AX to total H2AX (A), the quantity of γ-H2AX (pM) (B), or the quantity of total H2AX (pM per $1 \times 10^7$ cells/mL) (C) measured at various time points following treatment of MCF7 cells with vehicle (diamonds), 0.25 μM SN38 (squares), 1 μM AZD-6738 (triangles), a combination of 0.25 μM SN38 and 1 μM AZD-6738 (X), or a combination of 0.25 μM SN38 and 0.5 μM AZD-6738 (asterisks).
Figure 19:
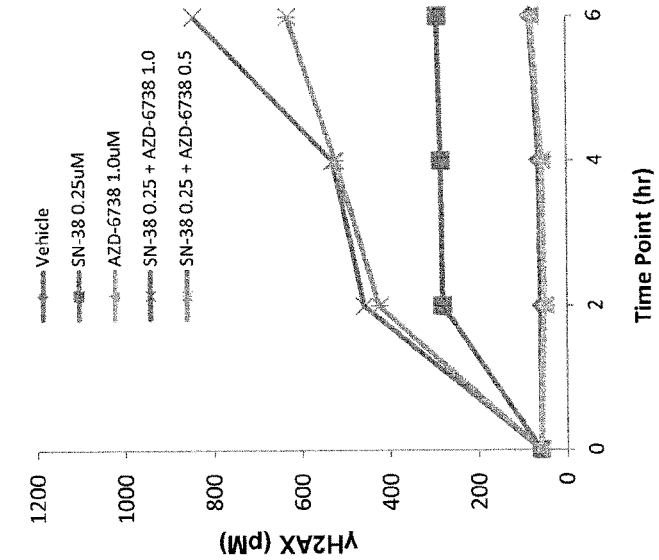
Figure 19:
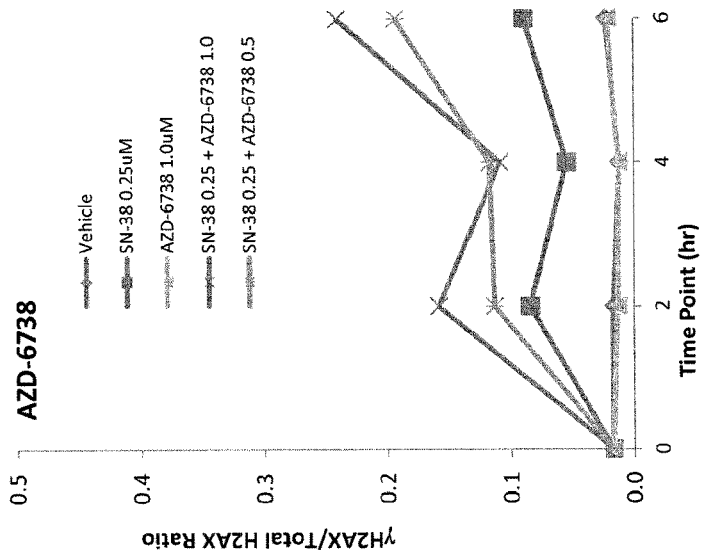
Figure 20:
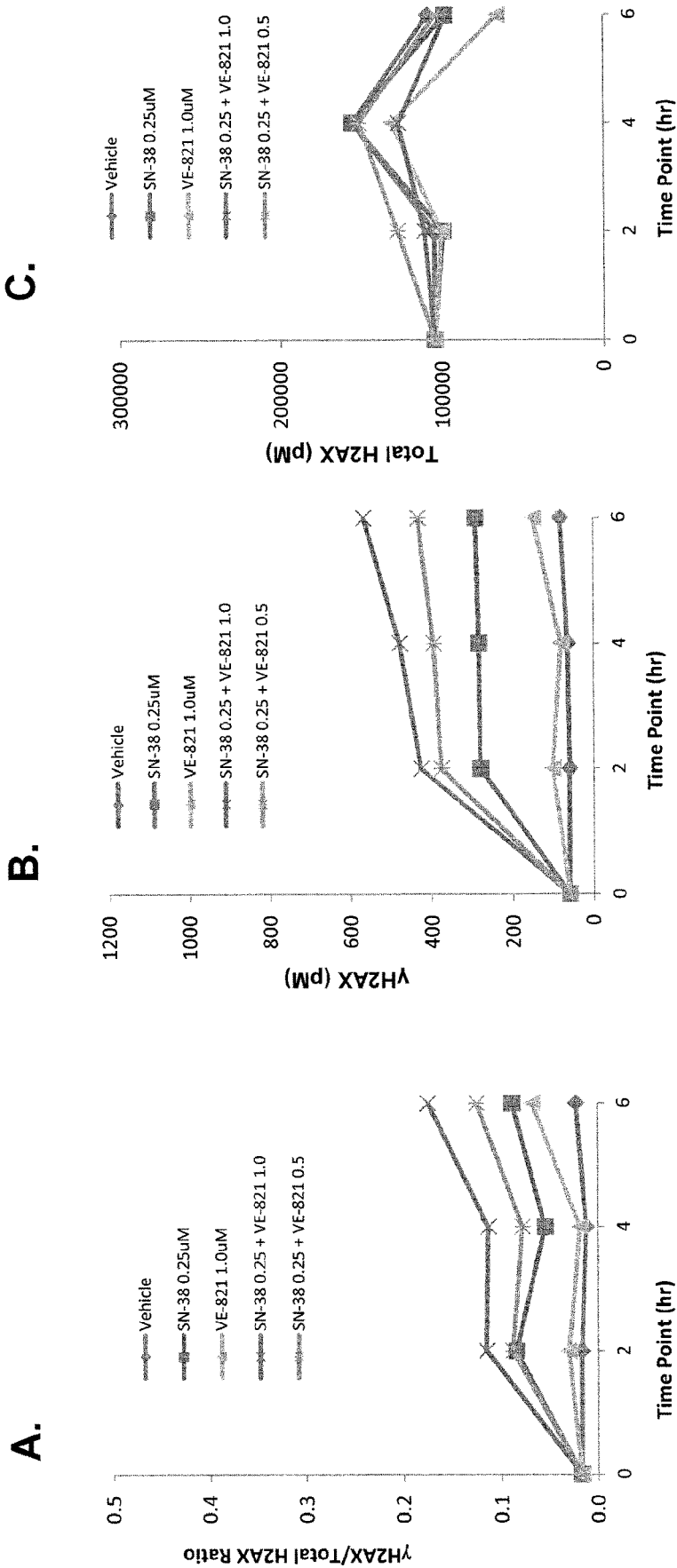
FIGS. 20A-20C are graphs showing the ratio of γ-H2AX to total H2AX (A), the quantity of γ-H2AX (pM) (B), or the quantity of total H2AX (pM per $1 \times 10^7$ cells/mL) (C) measured at various time points following treatment of MCF7 cells with vehicle (diamonds), 0.25 μM SN38 (squares), 1 μM VE-821 (triangles), a combination of 0.25 μM SN38 and 1 μM VE-821 (X), or a combination of 0.25 μM SN38 and 0.5 μM VE-821 (asterisks).
Figure 21:
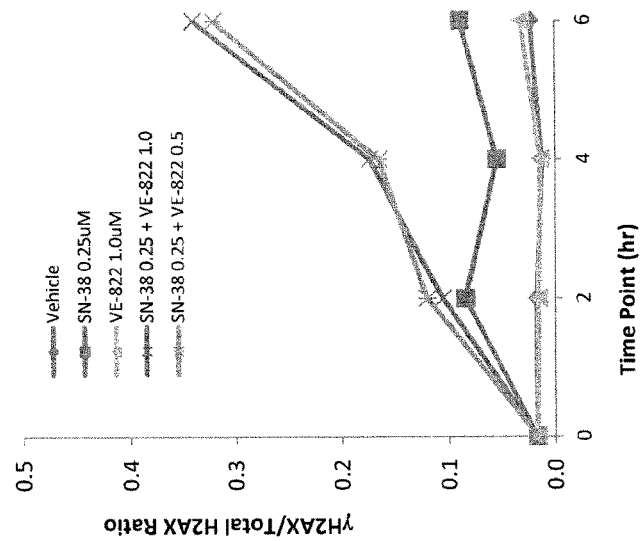
FIGS. 21A-21C are graphs showing the ratio of γ-H2AX to total H2AX (A), the quantity of γ-H2AX (pM) (B), or the quantity of total H2AX (pM per $1 \times 10^7$ cells/mL) (C) measured at various time points following treatment of MCF7 cells with vehicle (diamonds), 0.25 μM SN38 (squares), 1 μM VE-822 (triangles), a combination of 0.25 μM SN38 and 1 μM VE-822 (X), or a combination of 0.25 μM SN38 and 0.5 μM VE-822 (asterisks).
Figure 21:
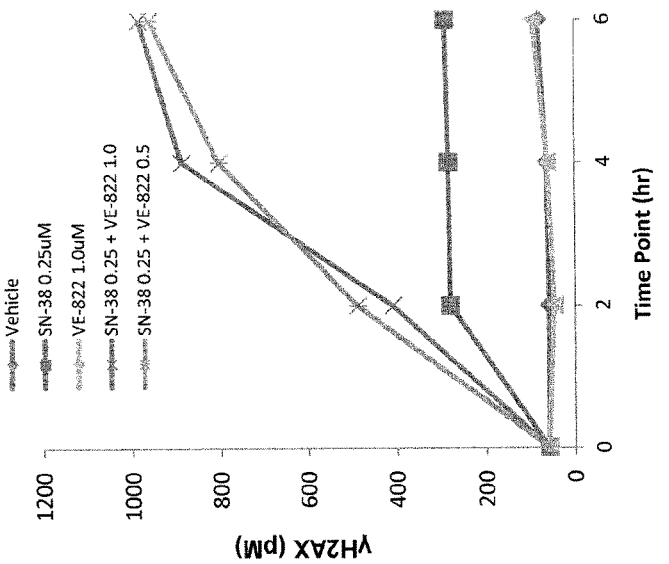
Figure 21:
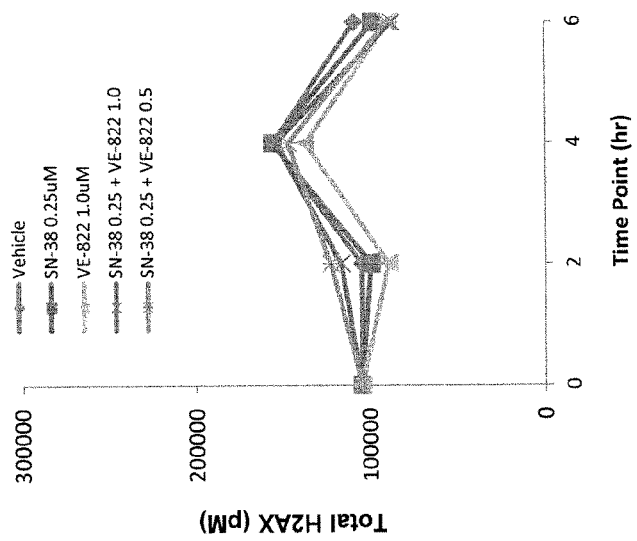
Figure 22:
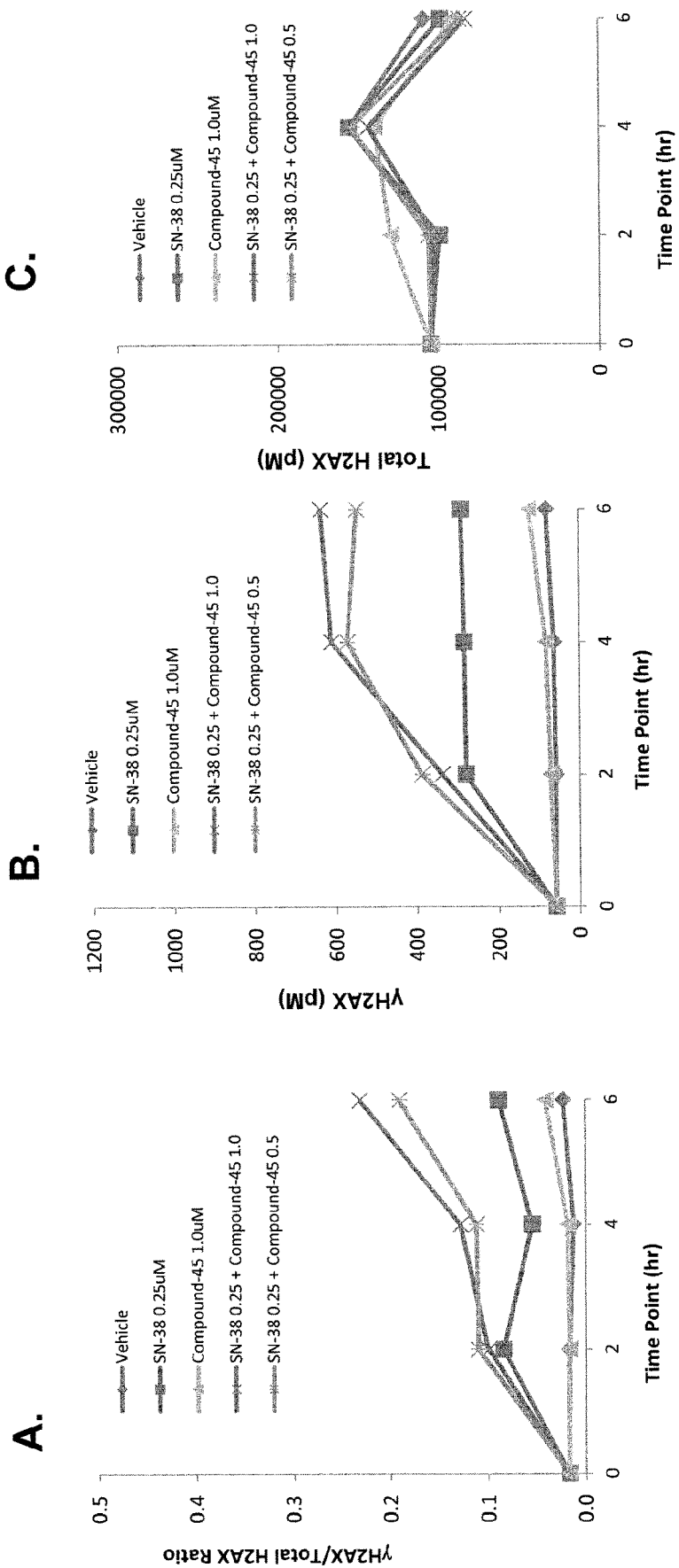
FIGS. 22A-22C are graphs showing the ratio of γ-H2AX to total H2AX (A), the quantity of γ-H2AX (pM) (B), or the quantity of total H2AX (pM per $1 \times 10^7$ cells/mL) (C) measured at various time points following treatment of MCF7 cells with vehicle (diamonds), 0.25 μM SN38 (squares), 1 μM Compound-45 (triangles), a combination of 0.25 μM SN38 and 1 μM Compound-45 (X), or a combination of 0.25 μM SN38 and 0.5 μM Compound-45 (asterisks).
Figure 23:
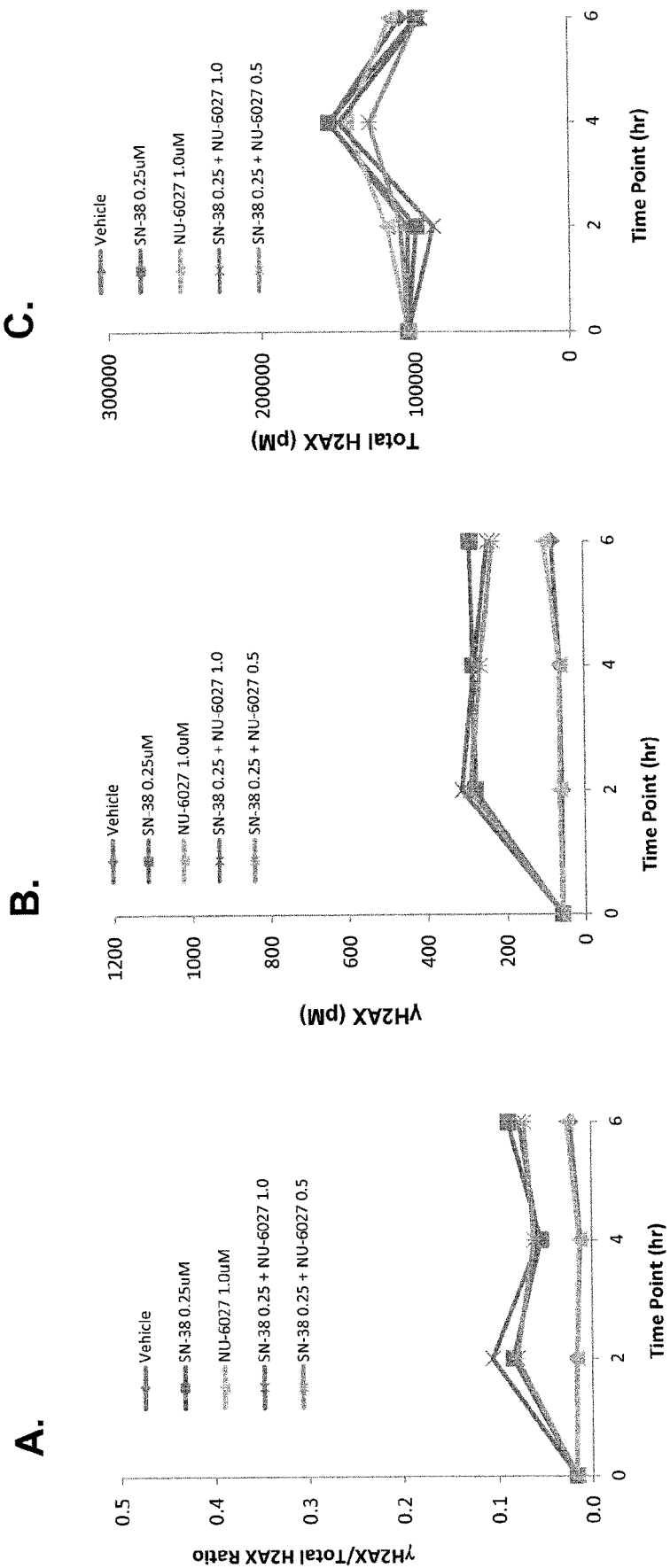
FIGS. 23A-23C are graphs showing the ratio of γ-H2AX to total H2AX (A), the quantity of γ-H2AX (pM) (B), or the quantity of total H2AX (pM per $1 \times 10^7$ cells/mL) (C) measured at various time points following treatment of MCF7 cells with vehicle (diamonds), 0.25 μM SN38 (squares), 1 μM NU-6027 (triangles), a combination of 0.25 μM SN38 and 1 μM NU-6027 (X), or a combination of 0.25 μM SN38 and 0.5 μM NU-6027 (asterisks).

MCF7 cells were treated with vehicle (control), SN38 (0.25 μM), ataxia-telangiectasia, a rad3-related protein (ATR) inhibitor (ATRi) (1 μM), a combination of SN38 (0.25 μM) and the ARTi (1 μM), or a combination of SN38 (0.25 μM) and the ARTi (0.5 μM). The ATR inhibitor was AZD-6738, VE-821, VE-822, Compound-45, or NU-6027. The treated cells were quantified for γ-H2AX and total H2AX using the immunoassays of Examples 1 and 2; respectively, and the ratio of γ-H2AX to total H2AX was determined. The results are shown in FIGS. 19A-19C (AZD-6738), FIGS. 20A-20C (VE-821), FIGS. 21A-21C (VE-822), FIGS. 22A-22C (Compound-45), and FIGS. 23A-23C (NU-6027). To independently confirm the presence of γ-H2AX, cells were concentrated by cytospin, and the cell lysate was stained using anti-γ-H2AX antibody. The stain was observed through a microscope. More intense staining was observed in the lysate from cells treated with a combination of SN38 and ATRi as compared to that from cells treated with SN38 or ATRi alone. No stain was observed in the lysate of cells treated with vehicle. Accordingly, the γ-H2AX antibody independently confirmed the presence of γ-H2AX in the treated cells.

As shown in FIGS. 19A-19C, FIGS. 20A-20C, FIGS. 21A-21C, FIGS. 22A-22C, and FIGS. 23A-23C, treatment with ATRi alone did not significantly induce formation of γ-H2AX. However, some combinations of the Top1 inhibitor SN38 with the ATRi led to synergistic induction of DNA DSB. Among the five ATR inhibitors evaluated in combination with the Top1 inhibitor SN38, VE-822 and AZD-6738 were observed to have the highest synergy for γ-H2AX induction, while NU-6027 showed none.

Example 17

This example demonstrates that the immunoassays of Examples 1 and 2 can be used to detect DNA DSB induced by treating tumor-bearing mice with drugs in vivo.

Figure 24:
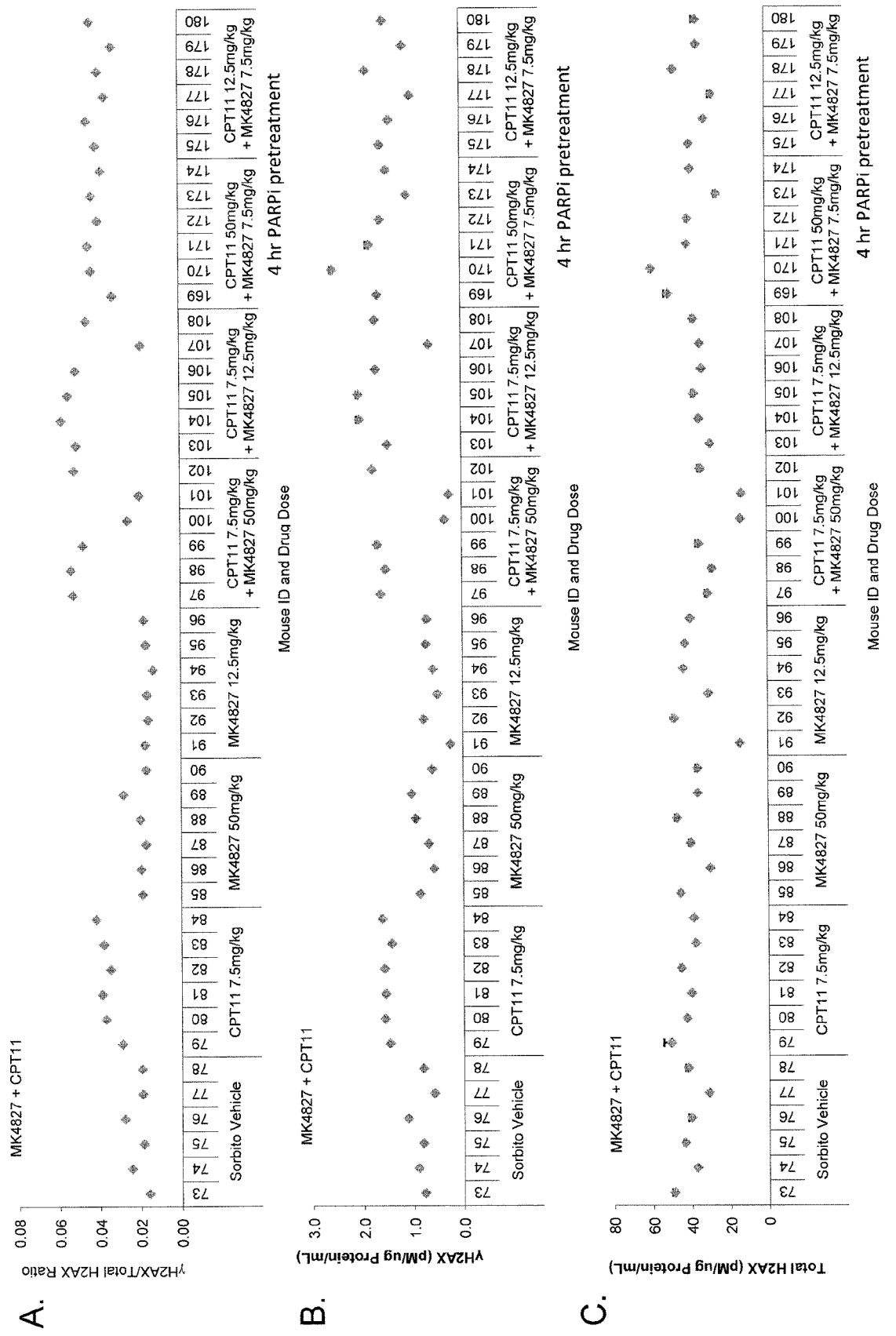
FIGS. 24A-24C are graphs showing the ratio of γ-H2AX to total H2AX (A), the quantity of γ-H2AX (pM) per μg protein (B), or the quantity of total H2AX (pM per μg protein) (C) measured in cell lysate isolated from A375 xenograft mouse models treated with vehicle (control), CPT-11 (7.5 mg/kg), MK4827 (50 mg/kg), MK4827 (12.5 mg/kg), a combination of CPT-11 (7.5 mg/kg) and MK4827 (50 mg/kg) administered simultaneously, a combination of CPT-11 (7.5 mg/kg) and MK4827 (12.5 mg/kg) administered simultaneously, MK4827 (7.5 mg/kg) administered four hours prior to CPT-11 (50 mg/kg), or MK4827 (7.5 mg/kg) administered four hours prior to CPT-11 (12.5 mg/kg).
Figure 25:
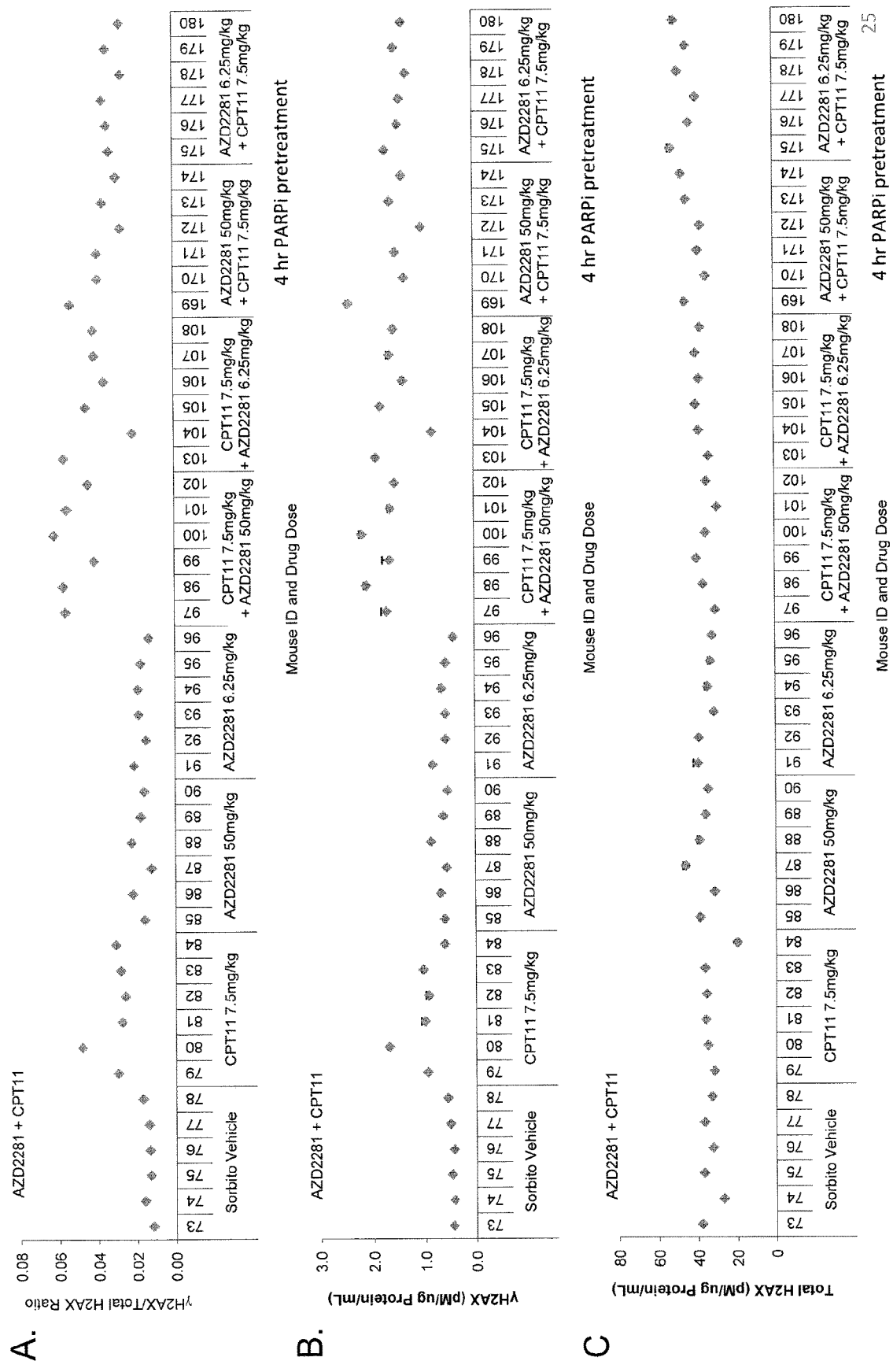
FIGS. 25A-25C are graphs showing the ratio of γ-H2AX to total H2AX (A), the quantity of γ-H2AX (pM) per μg protein (B), or the quantity of total H2AX (pM per μg protein) (C) measured in cell lysate isolated from A375 xenograft mouse models treated with vehicle (control), CPT-11 (7.5 mg/kg), AZD2281 (50 mg/kg), AZD2281 (6.25 mg/kg), a combination of CPT-11 (7.5 mg/kg) and AZD2281 (50 mg/kg) administered simultaneously, a combination of CPT-11 (7.5 mg/kg) and AZD2281 (6.25 mg/kg) administered simultaneously, AZD2281 (50 mg/kg) administered four hours prior to CPT-11 (7.5 mg/kg), or AZD2281 (6.25 mg/kg) administered four hours prior to CPT-11 (7.5 mg/kg).
Figure 26:
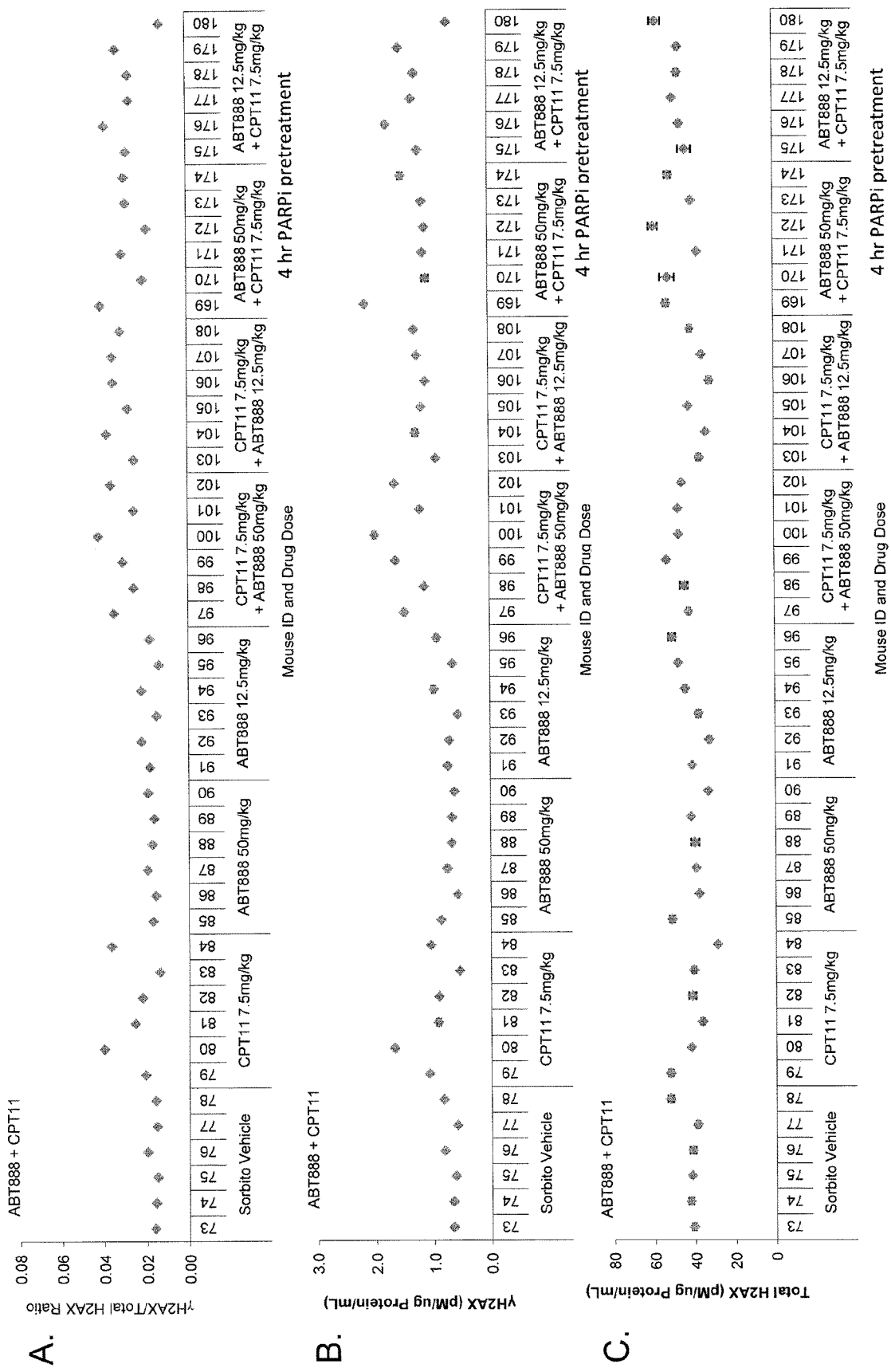
FIGS. 26A-26C are graphs showing the ratio of γ-H2AX to total H2AX (A), the quantity of γ-H2AX (pM) per μg protein (B), or the quantity of total H2AX (pM per pg protein) (C) measured in cell lysate isolated from A375 xenograft mouse models treated with vehicle (control), CPT-11 (7.5 mg/kg), ABT888 (50 mg/kg), ABT888 (12.5 mg/kg), a combination of CPT-11 (7.5 mg/kg) and ABT888 (50 mg/kg) administered simultaneously, a combination of CPT-11 (7.5 mg/kg) and ABT888 (12.5 mg/kg) administered simultaneously, ABT888 (7.5 mg/kg) administered four hours prior to CPT-11 (50 mg/kg) and, or ABT888 (7.5 mg/kg) administered four hours prior to CPT-11 (12.5 mg/kg).

A375 xenograft mouse models were treated with vehicle (control), CPT-11 alone, a PARP inhibitor alone, a combination of CPT-11 and the PARP inhibitor (PARPi) administered simultaneously, or a combination of CPT-11 and the PARPi, wherein the PARPi is administered four hours before CPT-11 is administered. CPT-11 is a modified version of CPT, also referred to as ironotecan (CAMPTOSAR). The PARP inhibitor was ABT-888, AZD-2281, or MK-4827. The dosages are shown in FIGS. 24A-24C, FIGS. 25A-25C, and FIGS. 26A-26C. Cells from the treated mice were quantified for γ-H2AX and total H2AX using the immunoassays of Examples 1 and 2, respectively, and the ratio of γ-H2AX to total H2AX was determined. The results are shown in FIGS. 24A-24C (MK4827), FIGS. 25A-25C (AZD2281), and FIGS. 26A-26C (ABT888).

As shown in FIGS. 24A-24C, FIGS. 25A-25C, and FIGS. 26A-26C, combinations of CPT-11 with ABT-888, AZD-2281 or MK-4827 caused synergistic induction of γ-H2AX, which indicates DNA DSB, in A375 xenografts in vivo.

Example 18

This example compares the detection of DNA DSB using a microscope immunofluorescence assay (IFA) to the detection of DNA DSB using the immunoassays (IA) of Examples 1 and 2.

Figure 27:
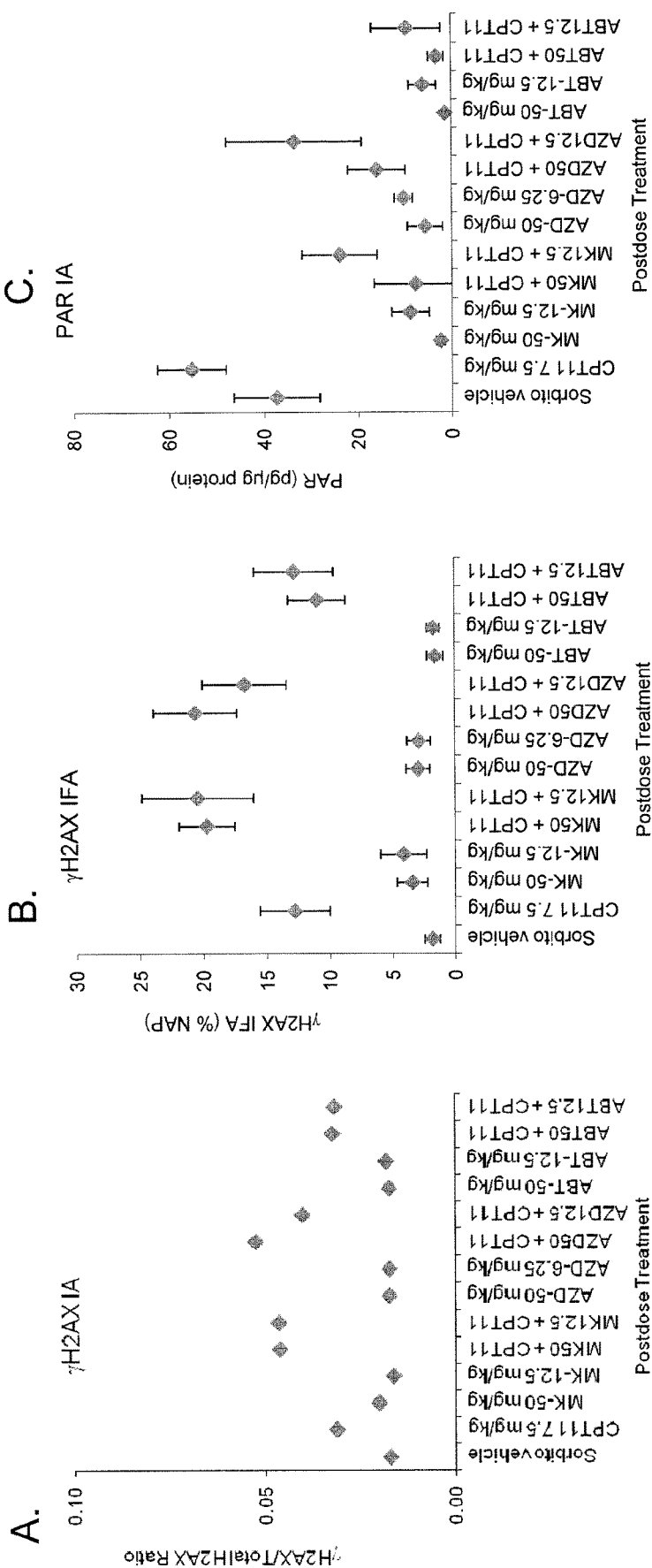
FIG. 27A is a graph showing the ratio of γ-H2AX to total H2AX measured by immunoassay (IA) in cells isolated from A375 xenograft mice that were treated with vehicle (control), CPT-11, ABT-888 (ABT), AZD-2281 (AZD), or MK-4827 (MK), a combination of CPT-11 with ABT-888, a combination of CPT-11 with AZD-2281, or a combination of CPT-11 with MK-4827, at the indicated dosages.
FIG. 27B is a graph showing the quantity of γ-H2AX measured by immunofluorescence assay (IFA) microscopy in cells isolated from A375 xenograft mice that were treated with vehicle (control), CPT-11, ABT-888 (ABT), AZD-2281 (AZD), or MK-4827 (MK), a combination of CPT-11 with ABT-888, a combination of CPT-11 with AZD-2281, or a combination of CPT-11 with MK-4827, at the indicated dosages.
FIG. 27C is a graph showing PAR inhibition (pg/μg protein/mL) measured by immunoassay (IA) in cells isolated from A375 xenograft mice that were treated with vehicle (control), CPT-11, ABT-888 (ABT), AZD-2281 (AZD), or MK-4827 (MK), a combination of CPT-11 with ABT-888, a combination of CPT-11 with AZD-2281, or a combination of CPT-11 with MK-4827, at the indicated dosages.

A375 xenograft mouse models were treated with vehicle (control), camptothecin-11 (CPT-11) alone, a PARP inhibitor alone, or a combination of CPT-11 and the PARP inhibitor at the dosages indicated in FIGS. 27A-27C. The PARP inhibitor was ABT-888, AZD-2281, or MK-4827. Cells from the treated mice were quantified for γ-H2AX and total H2AX using the immunoassays of Examples 1 and 2, respectively, and the ratio of γ-H2AX to total H2AX was determined. The results are shown in FIG. 27A.

The γ-H2AX in the cells from the treated mice was quantified by staining using a labeled anti-γ-H2AX antibody and counting the nuclear foci through a microscope. The results are shown in FIG. 27B. The ratio of γ-H2AX to total H2AX shown in FIG. 27A was comparable to the microscopy data, shown in FIG. 27B. PARP inhibition was confirmed by PAR ELISA (FIG. 27C).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of measuring the amount of exposure of a host to a DNA double-stranded break (DSB)-causing agent, the method comprising:

contacting (i) a first portion of a positive control biological sample and (ii) a first portion of a biological sample from the host with an antibody or antigen binding fragment thereof that specifically binds to gamma-H2AX (γ-H2AX, phosphorylated H2AX (histone family member X)) forms a first complex with the γ-H2AX that is present in each one of the positive control biological sample and the biological sample from the host;

contacting (i) a second portion of the positive control biological sample and (ii) a second portion of the biological sample from the host with an antibody or antigen binding fragment thereof that specifically binds to a histone H2A core protein and forms a second complex with the H2A core protein that is present in each one of the positive control biological sample and the biological sample from the host, wherein the positive control biological sample has been exposed to a known amount of the DSB-causing agent;

contacting the first and second complexes of the positive control biological sample and the biological sample from the host with an antibody or antigen binding fragment thereof that specifically binds to H2AX and forms a third complex with the H2AX in each of the first complex of the positive control biological sample and the first complex of the biological sample from the host and forms a fourth complex with the H2AX in each of the second complex of the positive control biological sample and the second complex of the biological sample from the host;

detecting each of the third and fourth complexes in the positive control biological sample and the biological sample from the host comprising a detectable label, comprising determining an amount of detectable label present in each of the positive control biological sample and the biological sample from the host;

quantifying each of the third and fourth complexes in the positive control biological sample and the biological sample from the host;

determining a ratio of the quantity of the third complex to the quantity of the fourth complex in the positive control biological sample;

determining a ratio of the quantity of the third complex to the quantity of the fourth complex in the biological sample from the host; and comparing the ratio of the quantity of the third complex to the quantity of the fourth complex in the positive control biological sample to the ratio of the quantity of the third complex to the quantity of the fourth complex in the biological sample from the host to determine the amount of exposure of the host to the DNA DSB-causing agent, wherein an increase in the ratio in the host biological sample as compared to the ratio in the positive control biological sample indicates that the DSB-causing agent has the ability to cause DNA DSBs in the host.

2. The method of claim 1, wherein the DNA DSB-causing agent is ionizing radiation (IR).

3. The method of claim 1, wherein the DNA DSB-causing agent is a drug.

4. The method of claim 1, wherein the DNA DSB-causing agent is an anti-cancer agent.

5. The method of claim 1, wherein the biological samples comprise cell lysates from no more than a single cell type.

6. The method of claim 1, wherein the biological samples comprise cell lysates from two or more cell types.

7. The method of claim 1, wherein the antigen binding fragment of the antibody that specifically binds to γ-H2AX is a Fab fragment (Fab), F(ab')2 fragment, diabody, triabody, tetrabody, single-chain variable region fragment (scFv), or disulfide-stabilized variable region fragment (dsFv).

8. The method of claim 1, wherein the antigen binding fragment of the antibody that specifically binds to the H2A core protein is a Fab fragment (Fab), F(ab')2 fragment, diabody, triabody, tetrabody, single-chain variable region fragment (scFv), or disulfide-stabilized variable region fragment (dsFv).

9. The method of claim 1, wherein the antigen binding fragment of the antibody that specifically binds to H2AX is a Fab fragment (Fab), F(ab')2 fragment, diabody, triabody, tetrabody, single-chain variable region fragment (scFv), or disulfide-stabilized variable region fragment (dsFv).

10. The method of claim 1, wherein the detectable label is an enzyme.

11. The method of claim 1, wherein the detectable label is a fluorescent molecule.

12. The method of claim 1, wherein the detectable label is a dye.

13. The method of claim 1, wherein the detectable label is biotin.

14. The method of claim 1, wherein the host is human.

15. The method of claim 1, wherein the host is human and γ-H2AX is phosphorylated at serine 139.

* * * * *

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Ser at position 1 is phosphorylated
<220> FEATURE:
<221> NAME/KEY: MISC_FEATURE
<222> LOCATION: (3)..(3)
<223> OTHER INFORMATION: X at position 3 is Asp, Glu, or Ala
<220> FEATURE:
<221> NAME/KEY: MISC_FEATURE
<222> LOCATION: (4)..(4)
<223> OTHER INFORMATION: X at position 4 is Ile, Leu, Tyr, or Phe

<400> SEQUENCE: 1

Ser Gln Xaa Xaa
1

<210> SEQ ID NO 2
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (27)..(27)
<223> OTHER INFORMATION: Ser at position 27 is phosphorylated

<400> SEQUENCE: 2
```

```
Ala Val Leu Leu Pro Lys Lys Thr Ser Ala Thr Val Gly Pro Lys Ala
1               5                   10                  15

Pro Ser Gly Gly Lys Lys Ala Thr Gln Ala Ser Gln Glu Tyr
            20                  25              30

<210> SEQ ID NO 3
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X at position 3 is Asp, Glu, or Ala
<220> FEATURE:
<221> NAME/KEY: MISC_FEATURE
<222> LOCATION: (4)..(4)
<223> OTHER INFORMATION: X at position 4 is Ile, Leu, Tyr, or Phe

<400> SEQUENCE: 3

Ser Gln Xaa Xaa
1

<210> SEQ ID NO 4
<211> LENGTH: 30
<212> TYPE: PRT
<213> ORGANISM: Artificial Sequence
<220> FEATURE:
<223> OTHER INFORMATION: Synthetic

<400> SEQUENCE: 4

Ala Val Leu Leu Pro Lys Lys Thr Ser Ala Thr Val Gly Pro Lys Ala
1               5                   10                  15

Pro Ser Gly Gly Lys Lys Ala Thr Gln Ala Ser Gln Glu Tyr
            20                  25              30
```